United States Patent [19]
Smith

[11] Patent Number: 6,042,601
[45] Date of Patent: Mar. 28, 2000

[54] APPARATUS FOR VASCULAR HOLE CLOSURE

[75] Inventor: Robert C. Smith, Ridgefield, Conn.

[73] Assignee: United States Surgical Corporation, Norwalk, Conn.

[21] Appl. No.: 09/044,048

[22] Filed: Mar. 18, 1998

[51] Int. Cl.⁷ ................................................. A61B 17/04
[52] U.S. Cl. ...................... 606/232; 606/139; 606/144; 606/148
[58] Field of Search .................. 606/139, 144, 606/148, 232

[56] References Cited

U.S. PATENT DOCUMENTS

| | | |
|---|---|---|
| 4,827,931 | 5/1989 | Longmore . |
| 4,935,027 | 6/1990 | Yoon ........................................ 606/146 |
| 5,171,257 | 12/1992 | Ferzli ....................................... 606/205 |
| 5,275,613 | 1/1994 | Haber et al. ............................. 606/205 |
| 5,275,614 | 1/1994 | Haber et al. ............................. 606/207 |
| 5,281,235 | 1/1994 | Haber et al. ............................. 606/139 |
| 5,282,806 | 2/1994 | Haber et al. ............................. 606/139 |
| 5,304,184 | 4/1994 | Hathaway et al. ...................... 606/144 |
| 5,318,578 | 6/1994 | Hasson .................................... 606/139 |
| 5,320,632 | 6/1994 | Heidmueller ............................ 606/144 |
| 5,364,408 | 11/1994 | Gordon .................................... 606/144 |
| 5,374,275 | 12/1994 | Bradley et al. .......................... 606/144 |
| 5,391,182 | 2/1995 | Chin ......................................... 606/213 |
| 5,417,699 | 5/1995 | Klein et al. .............................. 606/144 |
| 5,454,822 | 10/1995 | Schöb et al. ............................. 606/148 |
| 5,462,560 | 10/1995 | Stevens .................................... 606/144 |
| 5,462,561 | 10/1995 | Voda ........................................ 606/144 |
| 5,476,469 | 12/1995 | Hathaway et al. ...................... 606/144 |
| 5,499,990 | 3/1996 | Schülken et al. ........................ 606/144 |
| 5,503,634 | 4/1996 | Christy .................................... 606/144 |
| 5,507,755 | 4/1996 | Gresl et al. .............................. 606/139 |
| 5,527,322 | 6/1996 | Klein et al. .............................. 606/144 |
| 5,573,540 | 11/1996 | Yoon ........................................ 606/144 |
| 5,575,800 | 11/1996 | Gordon .................................... 606/144 |
| 5,578,044 | 11/1996 | Gordon et al. ........................... 606/144 |
| 5,578,057 | 11/1996 | Wenstrom, Jr. ......................... 606/232 |
| 5,720,757 | 2/1998 | Hathaway et al. ...................... 606/144 |

*Primary Examiner*—Gary Jackson

[57] ABSTRACT

An apparatus for facilitating wound closure of an opening in tissue includes a handle portion dimensioned to be gripped by the hand of a user, an elongate body portion connected to the handle portion and extending distally therefrom, a jaw mechanism including a stationary jaw affixed to the distal end portion of the elongate body portion and a movable jaw movably mounted to the distal end portion of the elongate body portion and movable between an initial closed position and a deployed open position, a suture assembly including a length of suture supported by the jaw mechanism, and being at least partially positionable within the opening in the tissue, first and second suture engaging members respectively operatively associated with the stationary jaw and the movable jaw, a deployment mechanism operable to move the movable jaw between the initial position and the deployed position, and an actuator mechanism operatively associated with the first and second suture engaging members and configured to move the first and second suture engaging members from a first position remote from the free ends of the suture to a second position wherein the first and second suture engaging members engage respective free ends of the suture. A method for facilitating closure of an opening in a tissue, e.g., a blood vessel wall is also disclosed.

17 Claims, 21 Drawing Sheets

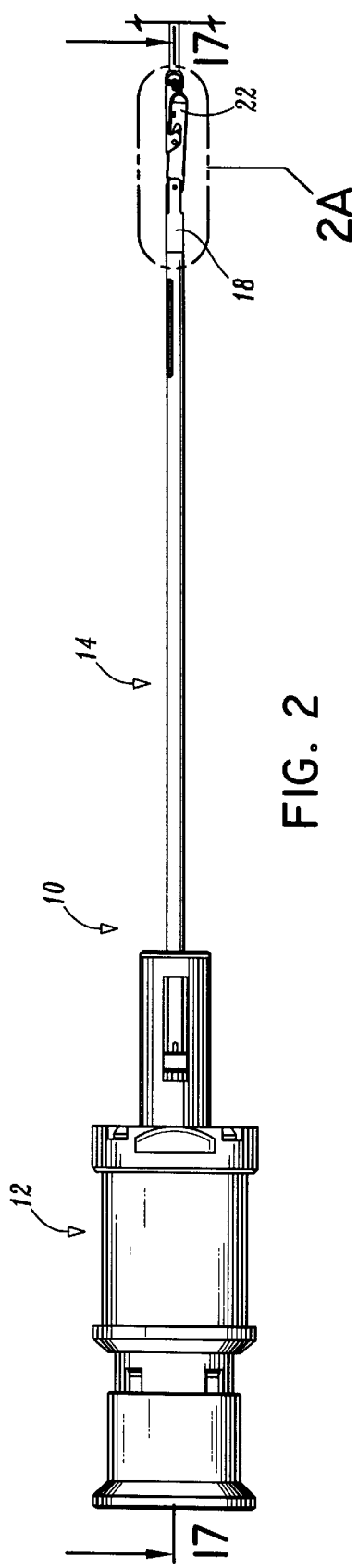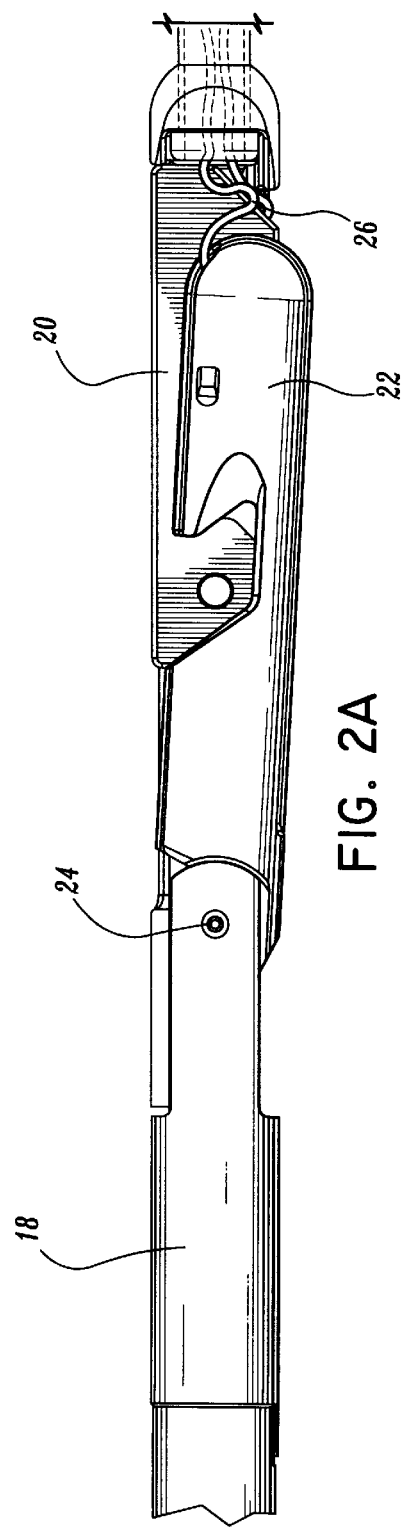
FIG. 2
FIG. 2A

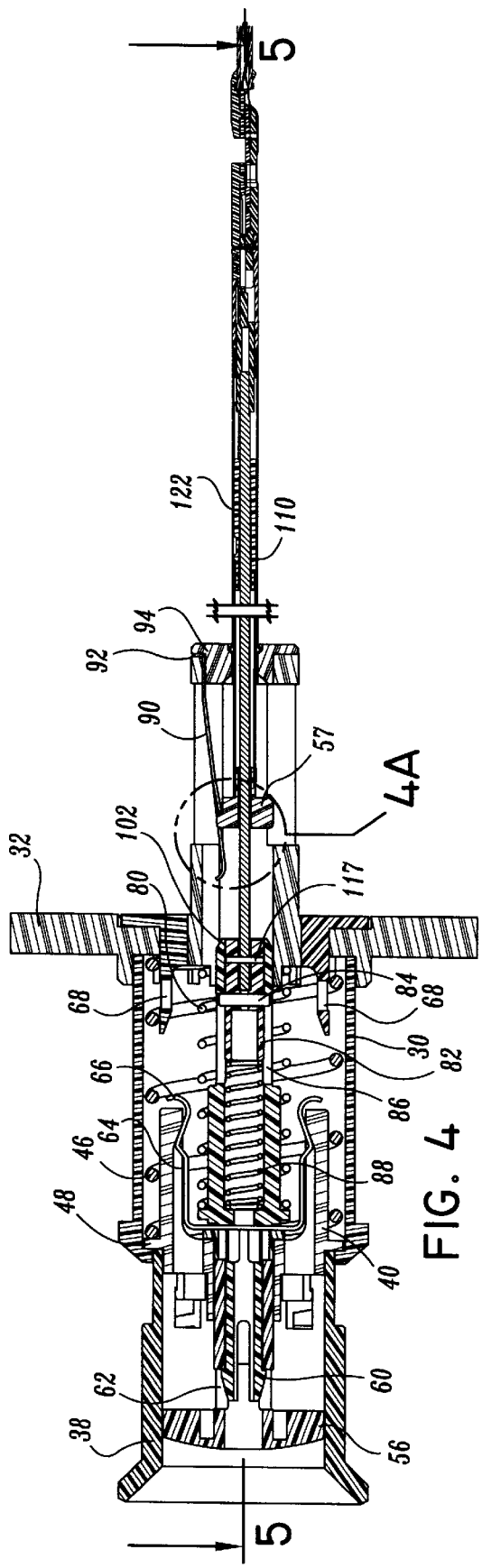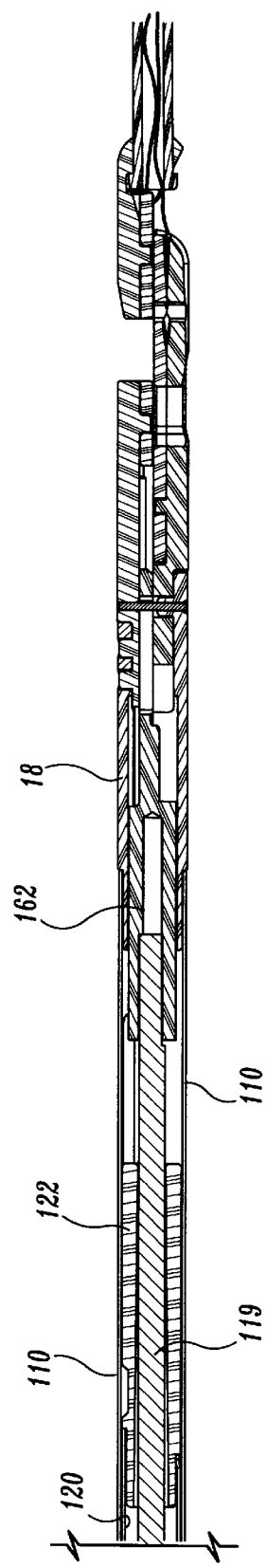

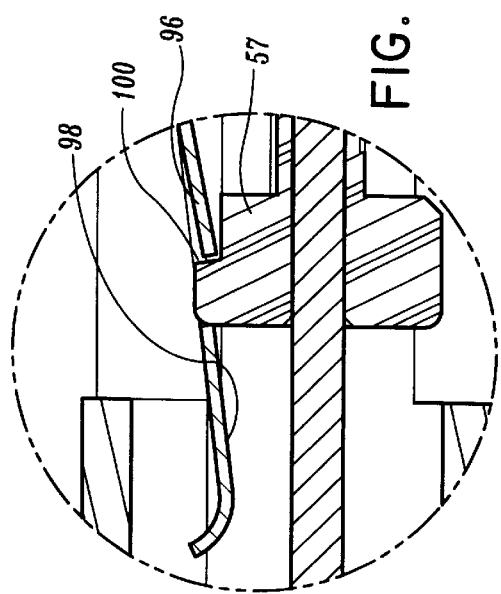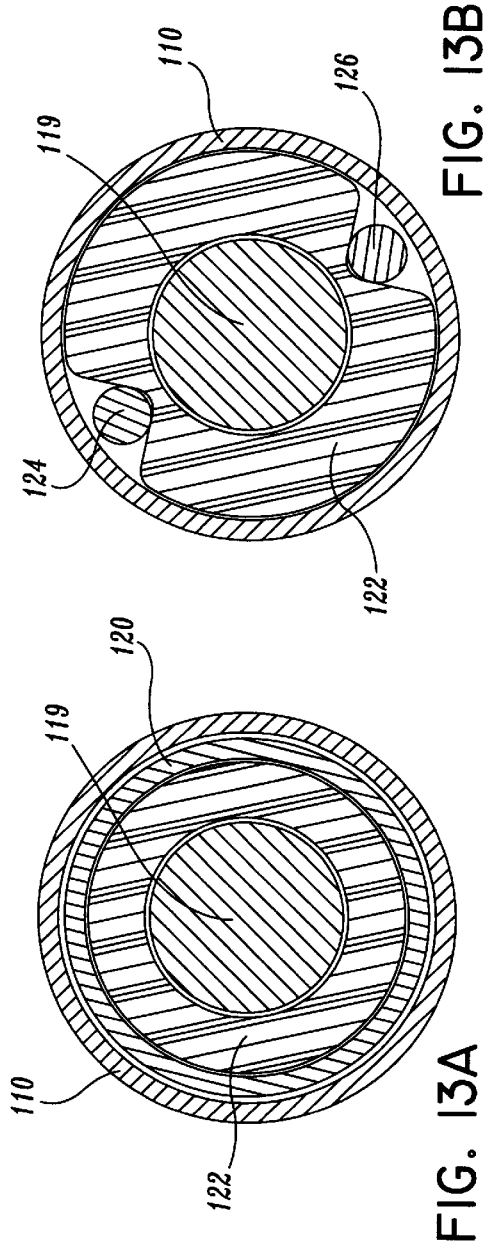

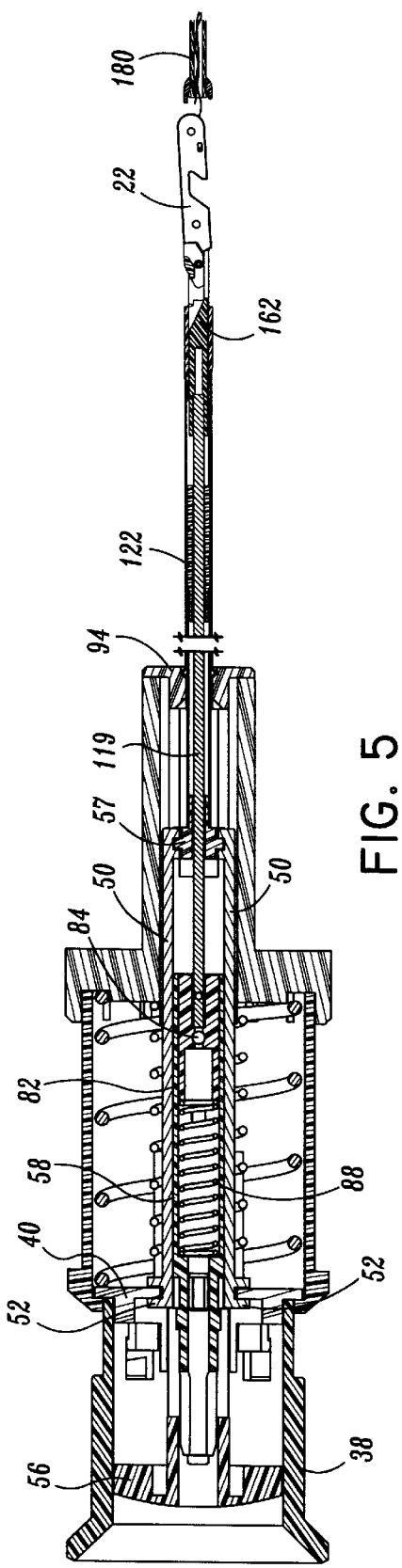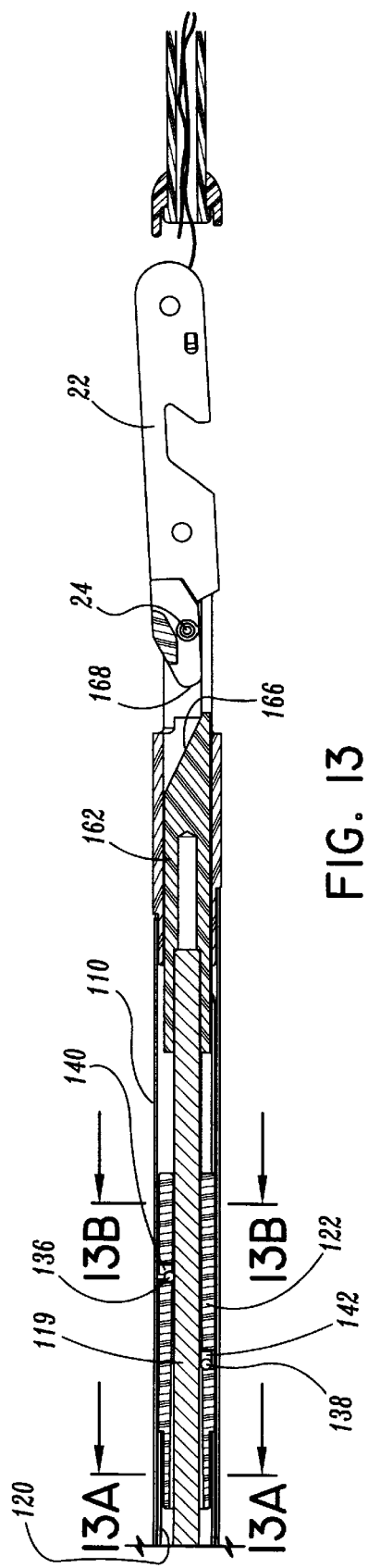

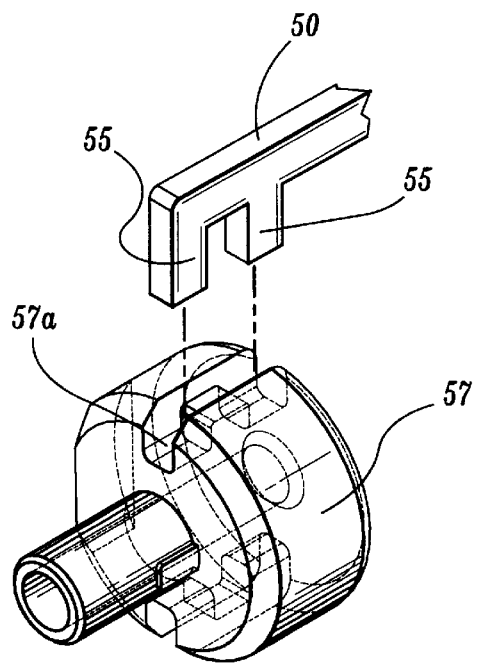
FIG. 6A
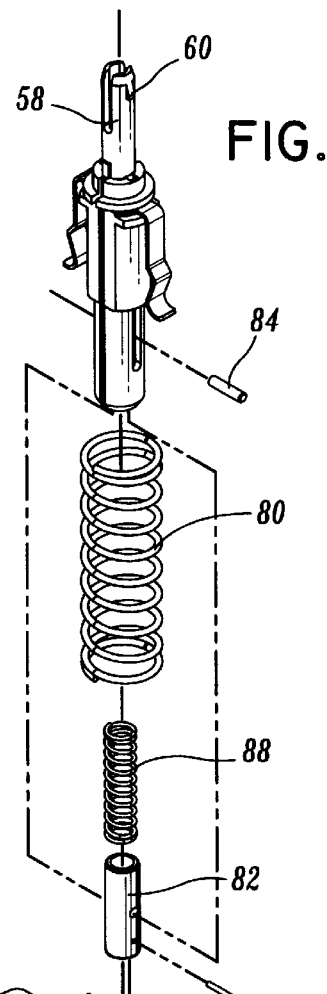
FIG. 6
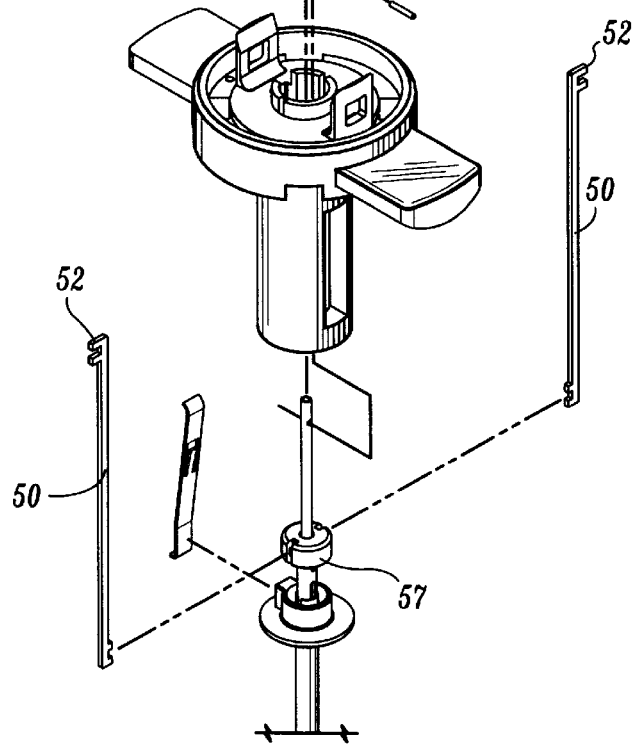

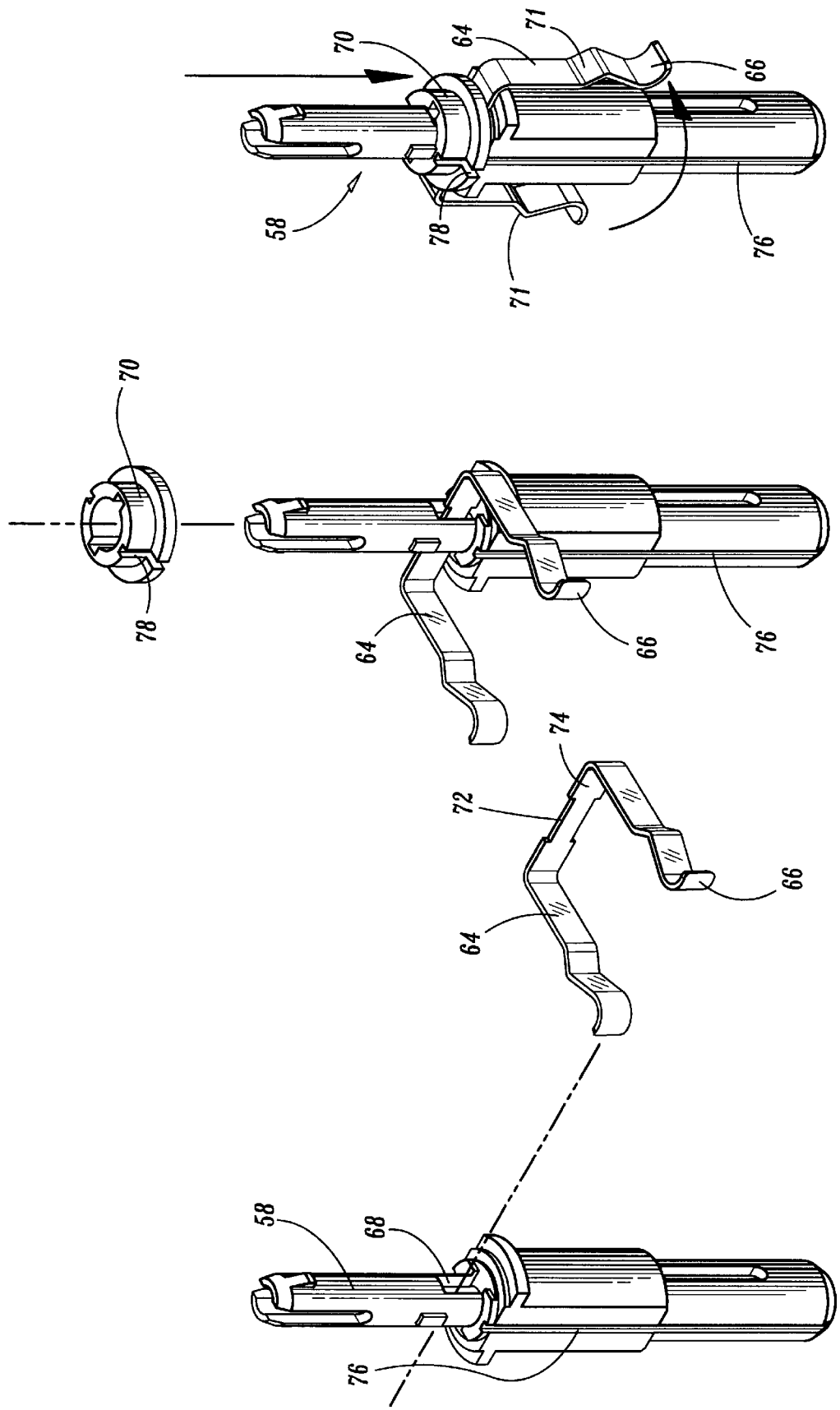

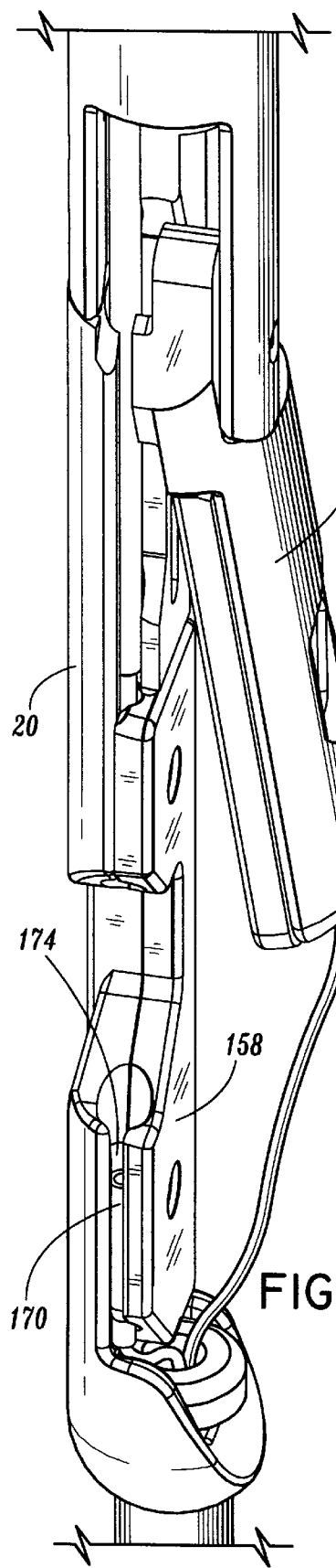
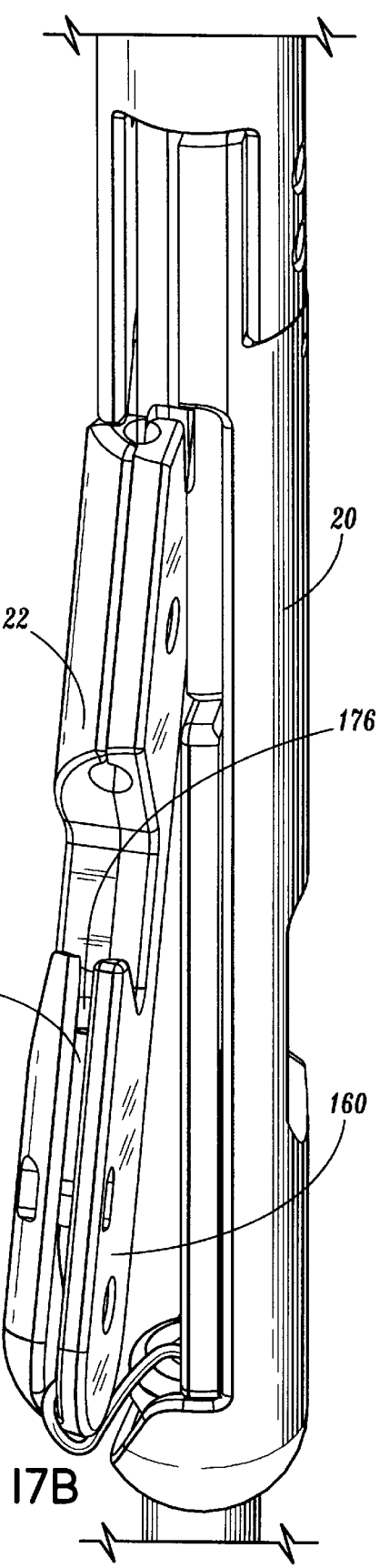
FIG. 17A
FIG. 17B

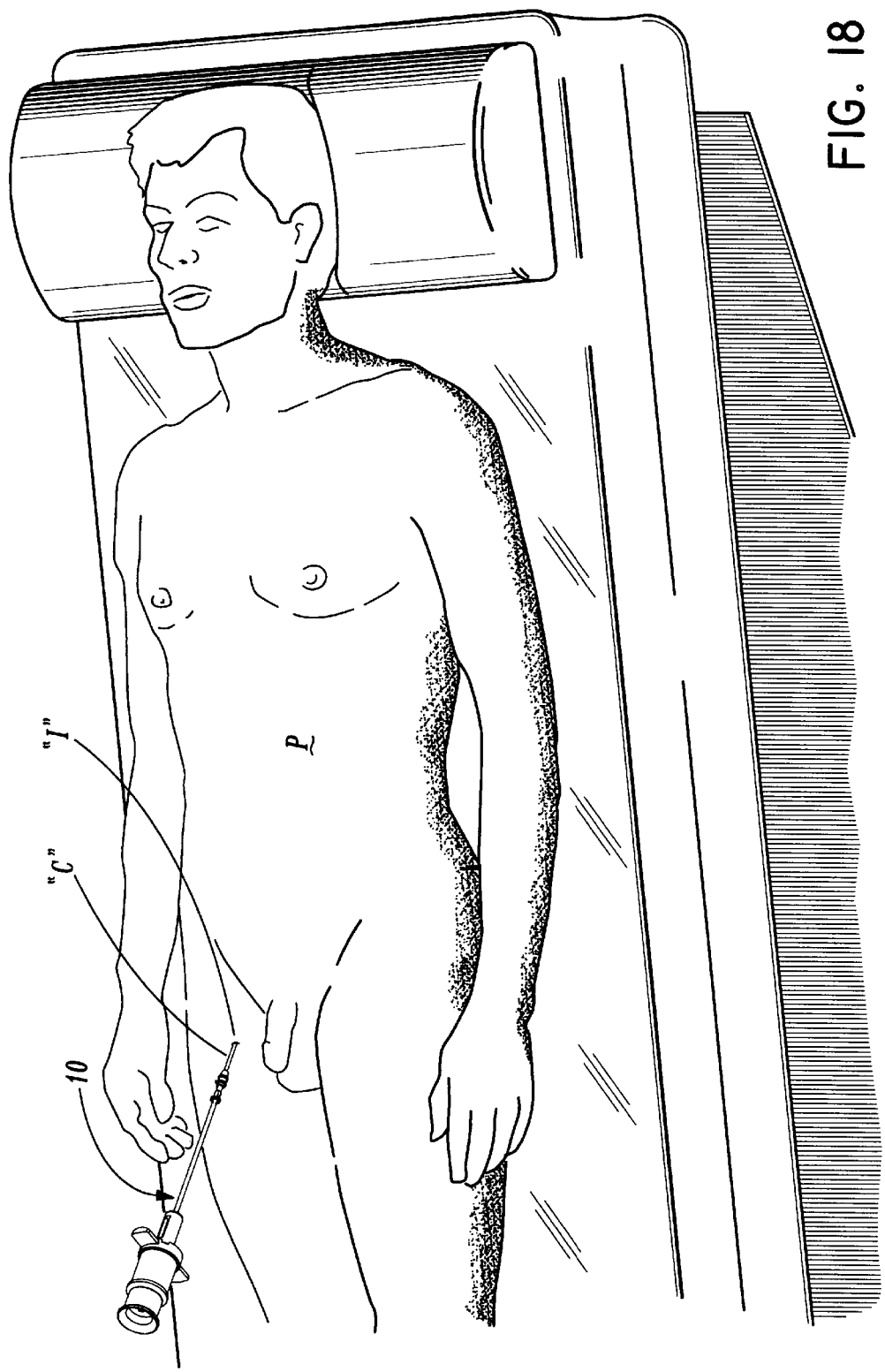

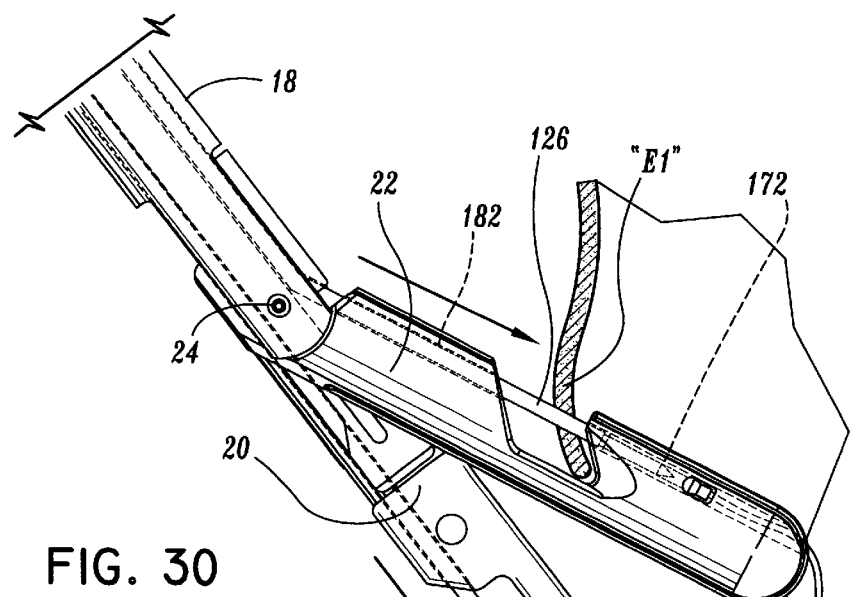
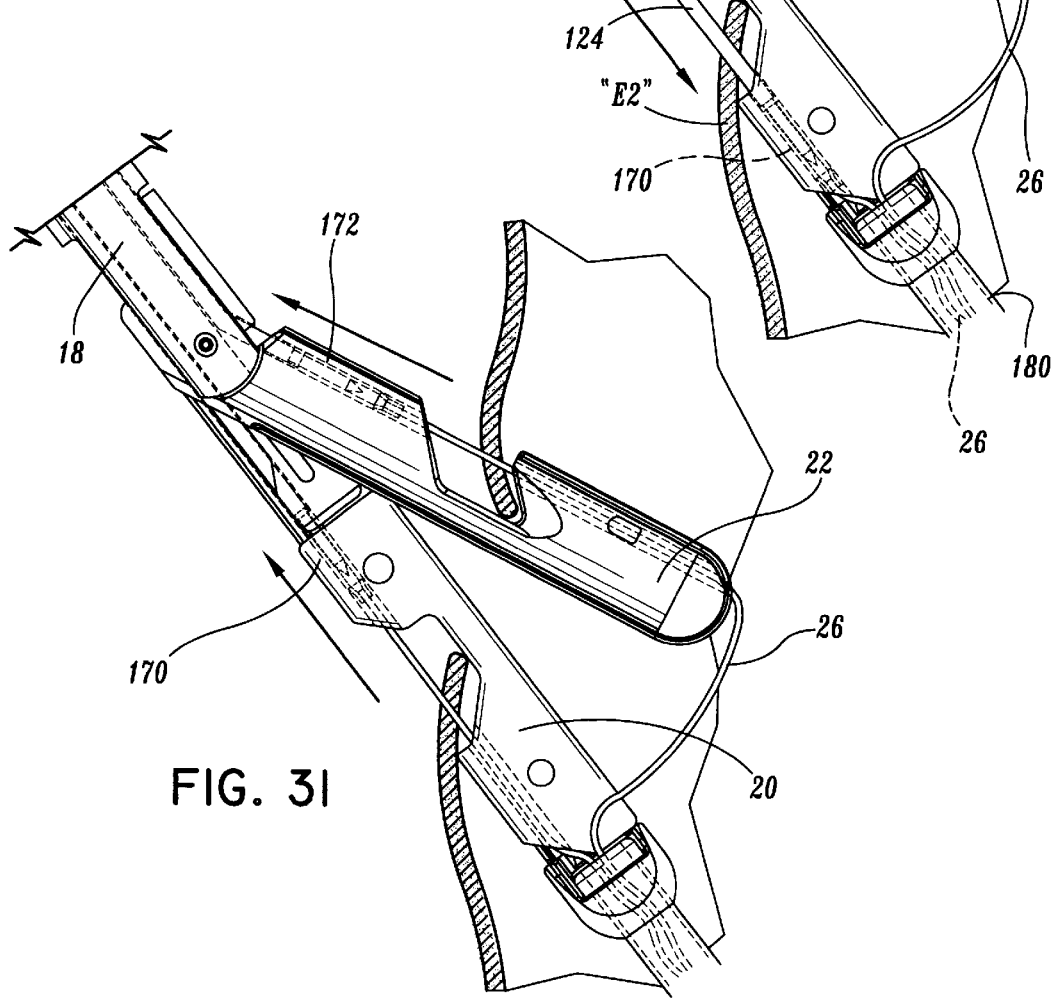
FIG. 30
FIG. 31

APPARATUS FOR VASCULAR HOLE CLOSURE

BACKGROUND

1. Technical Field

The present disclosure relates to an apparatus and method for closing a hole or puncture in a blood vessel, and, more particularly, to an apparatus for applying a suture assembly to a blood vessel to close a hole formed therein during an intravascular catheterization procedure.

2. Background of the Related Art

When performing a catheterization procedure such as, for example, an angiography or angioplasty, a sharpened hollow needle is first percutaneously introduced into the vascular system. A guide wire is then inserted through the hollow needle and into the lumen of a selected blood vessel. Subsequently, the needle is removed and a dilator and/or introducer is fed into the vessel along the guide wire. The guide wire is then removed and a suitable catheter is fed through the lumen of the introducer and advanced through the vascular system until the working end thereof is positioned at the operating site. At the conclusion of the catheterization procedure, the catheter is withdrawn, and subsequently, the dilator and/or introducer is also removed from the wound.

At this point in the procedure, the vessel puncture must be sealed in order to stem the flow of blood therethrough. Because it is often common practice to administer a blood thinning agent to the patient prior to the catheterization procedures, stemming the blood flow can be troublesome. A common method of healing the wound is to maintain external pressure over the vessel until the puncture naturally seals. This method of puncture closure typically takes about thirty minutes, with the length of time usually being greater if the patient is hypertensive or anti-coagulated.

When hand pressure is utilized, it can be uncomfortable for the patient and can use costly professional time on the part of the hospital staff. Other pressure application techniques, such as pressure bandages, sandbags or clamps, have been employed, but these devices also require the patient to remain motionless for an extended period of time and the patient must be closely monitored to ensure their effectiveness.

Other devices have been disclosed that plug or otherwise provide an obstruction in the area of the puncture. See, for example, U.S. Pat. Nos. 4,852,568 and 4,890,612, wherein a collagen plug is disposed in the blood vessel opening. When the plug is exposed to body fluids, it swells to create a block for the wound in the vessel wall. A potential problem of plugs introduced into the vessel is that particles may break off and float downstream to the point where they may lodge in a smaller vessel, causing an infarct to occur. Collagen material also acts as a nidus for platelet aggregation and, therefore, can cause intraluminal deposition of hemostatic agent, thereby creating the possibility of a thrombosis at the puncture site. Other plug-like devices are disclosed, for example, in U.S. Pat. Nos. 5,342,393; 5,370,660; and 5,411,520.

U.S. Pat. No. 5,417,699 to Klein et al. discloses a suture applying device for the percutaneous suturing of a vascular puncture site. The Klein '699 device includes a shaft which carries a pair of needles at its distal end. The needles are joined by a length of suture. The shaft is used to both introduce the needles within the lumen of the vessel and to draw the needle back through the vessel wall leaving a loop of suture behind to close the puncture site.

U.S. Pat. No. 5,527,322 to Klein et al. also discloses a suture applying device including a shaft having a nose piece attached at its distal end. A needle entry lumen in the shaft permits a flexible needle to be introduced in the distal direction. The deployed needle penetrates the tissue and enters a return lumen in the nose piece. The return lumen is U-shaped and acts to bend the flexible needle as it is advanced. In this way, the needle passes from the nose piece on the opposed side of a site. The needle then exits from the device, permitting the suture attached to the needle to be drawn fully through the device. The suture may then be tied in order to close and seal the tissue penetration.

Although the Klein '699 and Klein '322 devices offer several advantages in the closure of vascular openings, there are several shortcomings inherent to these devices which detract from their usefulness. In particular, the devices are generally complex requiring a multitude of moving parts and components. In addition, the Klein '699 device requires both needles to be complete introduced within the lumen of the blood vessel to be subsequently drawn through the vessel wall. This approach may not always be feasible or practical due to the limited accessibility of certain vessels.

SUMMARY

The present disclosure relates to an apparatus for facilitating wound closure of an opening in tissue. The apparatus includes a handle portion dimensioned to be gripped by the hand of a user, an elongate body portion connected to the handle portion and extending distally therefrom, a jaw mechanism including a stationary jaw affixed to the distal end portion of the elongate body portion and a movable jaw movably mounted to the distal end portion of the elongate body portion and being movable between an initial closed position and a deployed open position, a suture assembly including a length of suture supported by the jaw mechanism and being at least partially positionable within the opening in the tissue, first and second suture engaging members respectively operatively associated with the stationary jaw and the movable jaw, a deployment mechanism operable to move the movable jaw between the initial position and the deployed position, and an actuator mechanism operatively associated with the first and second suture engaging members and configured to move the first and second suture engaging members from a first position remote from the free ends of the suture to a second position wherein the first and second suture engaging members engage respective free ends of the suture.

In a preferred embodiment, a lockout mechanism is operatively associated with the deployment mechanism and operatively engageable with the actuator mechanism to prevent premature actuation of the actuator mechanism. The lockout member is movable to a release position disengaged from the actuator mechanism upon movement of the jaw mechanism to the deployed position to thereby permit actuation of the actuator mechanism.

The deployment mechanism may include a latch member engagable with one of the handle and the elongate body portion to maintain the movable jaw in the deployed position. The latch member is adapted to release the one of the handle and the elongate body portion upon movement of the first and second suture engaging members to the second position. Preferably, the actuator mechanism includes camming structure operatively engagable with the latch member such that the camming structure disengages the latch member from the one of the handle and the elongate body portion upon movement of the first and second suture engaging members to the second position.

A deployment biasing member is provided to normally bias the deployment mechanism to a position corresponding to the initial position of the movable jaw.

The suture assembly preferably includes a ferrule attached to each suture end portion. A first ferrule is mounted to the stationary jaw and a second ferrule is mounted to the movable jaw. The first and second suture engaging members have pointed end portions to penetrate tissue. Preferably, the pointed end portions of the first and second suture engaging members are correspondingly dimensioned to be received within the ferrules of respective suture end portions such that the suture engaging members securely frictionally engage the ferrules, whereby upon proximal movement of the suture engaging members the suture end portions are pulled through the blood vessel wall.

A method for facilitating closure of an opening in a tissue is also disclosed.

BRIEF DESCRIPTION OF THE DRAWINGS

Preferred embodiments of the disclosure are described herein with reference to the drawings wherein:

FIG. 2 is a side elevational view of the apparatus of FIG. 1 with the jaw assembly in a non-deployed position;

FIG. 2A is an isolated view of FIG. 2 illustrating the jaw assembly and the suture assembly mounted to the jaw assembly;

FIG. 4 is a side cross-sectional view of the apparatus;

FIG. 4A is an isolated view of FIG. 4 illustrating the lockout structure to prevent actuation of the apparatus;

FIG. 5 is a cross-sectional view taken along the lines 5—5 of FIG. 4;

FIG. 6 is a perspective view with parts separated further illustrating components of the deployment assembly and actuator assembly;

FIG. 6A is an enlarged perspective view illustrating the drive bar and drive collar of the actuator assembly;

FIG. 7 is a perspective view illustrating an initial assembly stage of a latch mechanism for maintaining the jaw mechanism in a deployed position;

FIG. 8 is a perspective view illustrating an intermediate stage of the assembly of the latch mechanism;

FIG. 9 is a perspective view illustrating the latch mechanism in the assembled position;

FIG. 12 is an enlarged cross-sectional view of the distal end of the elongate body depicted in FIG. 4;

FIG. 13 is an enlarged cross-sectional view of the distal end of the elongated body depicted in FIG. 5;

FIG. 13A is a sectional view taken along lines 13A—13A of FIG. 13;

FIG. 13B is a sectional view taken along lines 13B—13B of FIG. 13;

FIGS. 17A–17B are perspective views of the jaw assembly of FIG. 16;

FIG. 18 is a perspective view illustrating percutaneous insertion of the apparatus of FIG. 1 into the femoral artery of a patient in accordance with the preferred method of the present disclosure;

FIG. 30 is a side view, partially shown in section, illustrating the jaw assembly in a deployed position and the suture engaging members penetrating the wall of the femoral artery to engage the suture ferrules of the suture assembly;

FIG. 31 is a view similar to FIG. 30 illustrating retraction of the needle engaging members, suture ferrules and length of suture through the wall of the femoral artery;

DETAILED DESCRIPTION OF THE PREFERRED EMBODIMENTS

Figure 1:
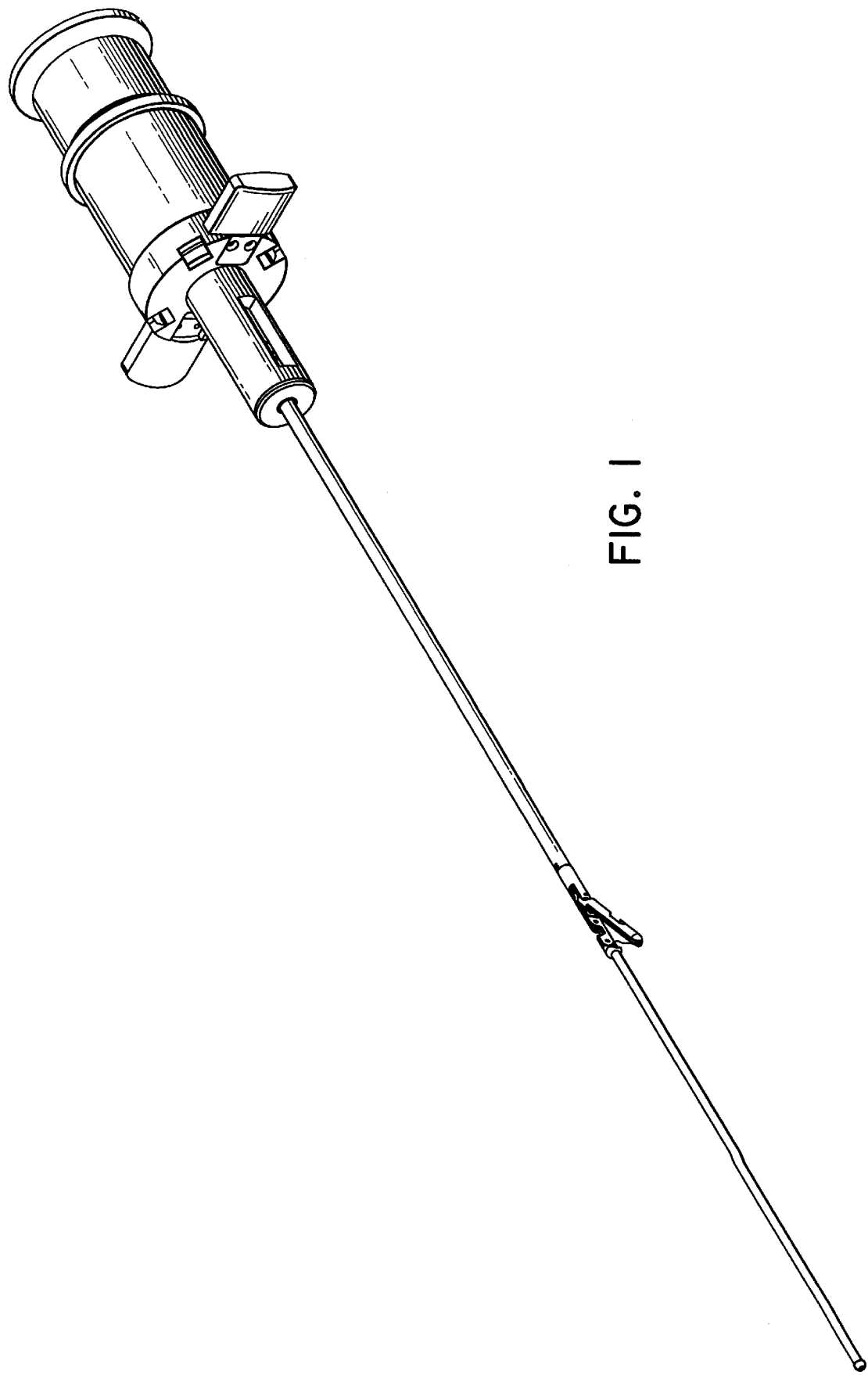
FIG. 1 is a perspective view of a surgical apparatus constructed in accordance with the principles of the present disclosure illustrating a handle, an elongate body extending from the handle and a jaw assembly disposed at the distal end of the elongate body and in a deployed position.

In general, an objective of the apparatus is to deploy a suture assembly about an opening formed in a blood vessel wall, during, e.g., a catheterization procedure, to facilitate closing of the opening to stem the flow of blood therethrough. In the drawings and in the description which follows, the term "proximal", as is traditional, will refer to that end of the apparatus, or component thereof, which is closer to the operator, while the term "distal" will refer to that end of the apparatus, or component thereof, which is more remote from the operator.

Referring now to FIGS. 1, 2 and 2A, surgical apparatus 10 generally includes a handle 12, an elongate body 14 connected to and extending distally from the handle 12 and a jaw mechanism 16 mounted at the distal end of the elongate body 14. Jaw mechanism 16 is mounted to cylindrical jaw support 18 and has a first stationary jaw member 20 and a second movable jaw member 22 movably mounted to the jaw support 18 about pivot pin 24. Movable jaw 22 pivots between a closed position depicted in FIG. 2A and an open position depicted in FIG. 1. Jaw mechanism 16 supports a length of suture 26 utilized to close the opening in the vessel wall as will be described in greater detail hereinbelow.

Figure 3:
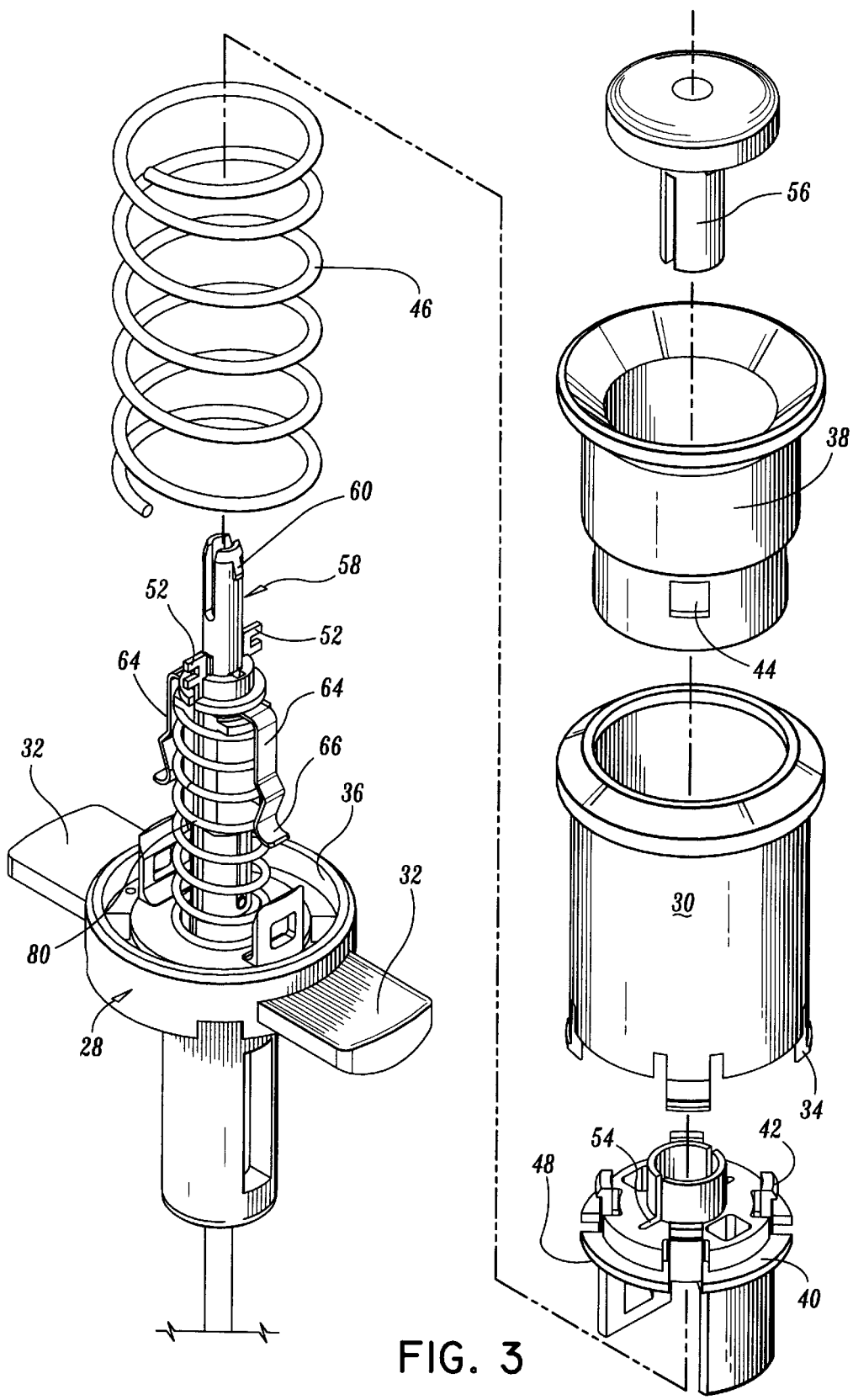
FIG. 3 is an enlarged perspective view with parts separated of the handle illustrating the components of the actuator assembly for actuating the suture engaging assembly and the deployment assembly for deploying the jaw assembly.

With reference now to FIGS. 3–5, in conjunction with FIG. 1, handle 12 includes handle base 28 and handle cover 30 fixedly mounted to the handle base 28. Handle base 28 includes diametrically opposed wing portions 32 which are dimensioned to be grasped by the user. Handle cover 30 possesses a plurality of circumferentially spaced locking tabs 34 which lockingly engage a peripheral ledge 36 of handle base 28 to secure the two components to each other. Handle 12 further includes actuator 38 at least partially positioned within handle cover 30 and slidably movable therein. Actuator 38 is connected to actuator collar 40 through a tab and slot arrangement having a plurality of circumferential tabs 42 of actuator collar 40, which are received within correspondingly dimensioned openings 44 defined in the actuator 38. Actuator 38 is longitudinally movable to deploy a pair of suture engaging members or needles as will be discussed hereinbelow.

An actuator spring 46 is disposed within handle cover 30 and engages at one end handle base 28 and at its other end circumferential ledge 48 of actuating collar 40 to normally bias the collar 40 and, hence, actuator 38 to its proximal unactuated position depicted in FIG. 4.

As depicted in FIGS. 5, 6 and 6A, a pair of drive bars 50 are provided which at their proximal ends have fingers 52 to engage a pair of slots 54 (FIG. 3) formed in actuator collar 40 and at their distal ends have fingers 55 which engage slots 57a of a drive collar 57. Drive bars 50 and drive collar 57 are operatively connected to the suture engaging members and thus function in advancing the engaging members upon actuation or movement of actuator 38.

With reference again to FIGS. 3–5, handle 12 also possesses a deployment member 56 positioned within actuator 38. Deployment member or button 56 is configured to move the jaw mechanism 16 between the open and closed positions. Deployment member 56 is fixedly connected to deployment plunger 58. In a preferred embodiment, deployment plunger 58 has circumferential tabs 60 which engage correspondingly dimensioned openings 62 (FIG. 4) defined in the deployment member 56 to connect the two components. Deployment plunger 58 has a latch member 64 mounted thereto which functions in maintaining movable jaw 22 in the deployed position during actuation. In particular, latch member 64 has engaging end portions 66 which are received within correspondingly dimensioned latch recesses 68 defined in handle base 28 upon depression of deployment button 56 thus maintaining the button in its distal position.

FIGS. 7–9 illustrate the sequence of assembly of latch member 64 and deployment plunger 58. Latch member 64 is initially inserted through an opening 68 formed in deployment plunger 58. As shown in FIG. 7, once latch member 64 has been inserted through opening 68, a cap 70 is positioned over deployment plunger 58. With reference now to FIG. 8, latch member 64 is pivoted within opening 68 such that latch member 64 extends parallel to deployment plunger 58. Thereafter, cap 70 is slid downwardly to secure latch member 64 in position. Preferably, projections 72 formed on deployment plunger 58 secure cap 70 of latch member 64 in position. As shown in FIGS. 7 and 8, notches 72 formed in backspan 74 prevent latch member 64 from sliding transversely within opening 68.

Deployment plunger 58 additionally includes longitudinally extending grooves 76 which provide clearance and slidable reception of drive bars 50. Corresponding grooves 78 are also provided in cap 70. Deployment plunger 58 and hence deployment member 56 is biased to its initial proximal position by coil spring 80 (FIG. 4).

Referring now to FIGS. 4–6, deployment plunger 58 has deployment extension 82 slidably mounted within a longitudinal bore of the deployment plunger 58. A pin 84 is affixed to deployment extension 82 and rides within slots 86 formed in deployment plunger 58. A biasing spring 88 normally biases deployment extension 82 distally and is at least partially received within the bore defined in deployment plunger 58. Biasing spring 88 functions in biasing the movable jaw to the open or deployed position upon movement of the deployment member 56 to the distal position.

Figure 10:
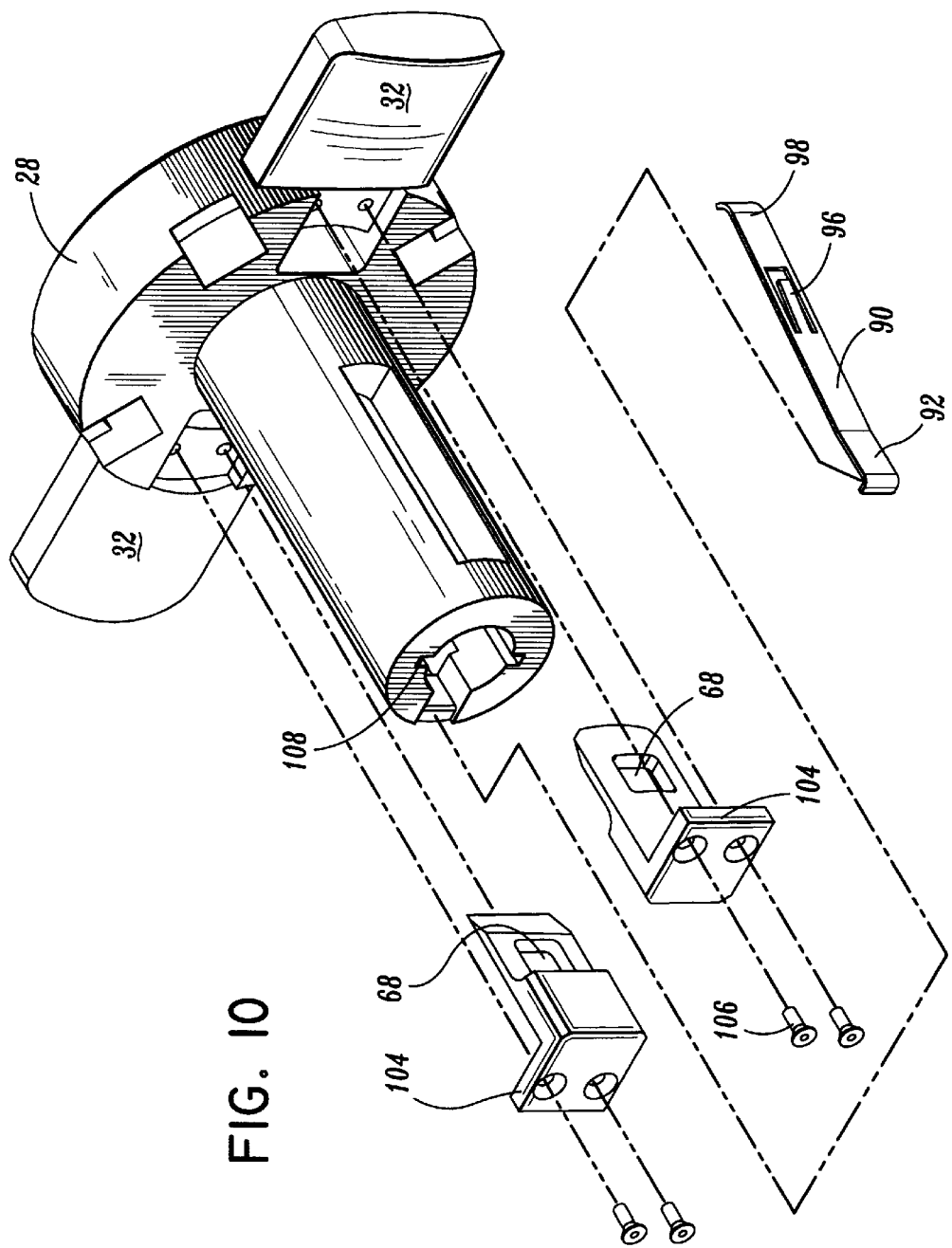
FIG. 10 is a perspective view with parts separated illustrating the handle base and a lockout member of the lockout structure depicted in FIG. 4A.

With reference to FIGS. 4, 4A and 10, handle base 28 includes a leaf spring 90 which extends generally longitudinally within the handle base. Leaf spring 90 functions as lockout structure to prevent actuation of actuator 38 until movable jaw 22 has been moved to a deployed position. Leaf spring 90 includes a distal lip portion 92 which sits within a correspondingly dimensioned slot defined between distal nose piece 94 (FIG. 4) and handle base 28 to positively fix the leaf spring 90 to the handle base 28. Nose piece 94 is connected to handle base 28 by conventional means. Leaf spring 90 additionally includes a projecting locking finger 96 and a camming surface 98 (FIG. 4A). Locking finger 96 is configured to engage corresponding structure (e.g. a ledge 100) on drive collar 57 thereby preventing actuation of surgical apparatus 10 until such time as movable jaw 22 has been moved to a deployed position. Upon movement of jaw 22 to a deployed position, camming surface 98 is engaged by a corresponding camming surface 102 (FIG. 4) on deployment plunger 58 to move locking finger 96 from its engagement with locking ledge 100 of drive collar 57.

As further shown in FIG. 10, handle base 28 includes latches 104 which are secured to handle base 28 by means of rivets 106. Alternatively, latches 104 may be affixed to handle base 28 by any other suitable means, such as, for example spot welds, screws, glues, etc. Latches 104 define latch recess openings 68 which receive end portions 66 of latch member 64 (FIG. 4). Handle base 28 also includes a pair of grooves 108 to guide drive bars 50.

Figure 11:
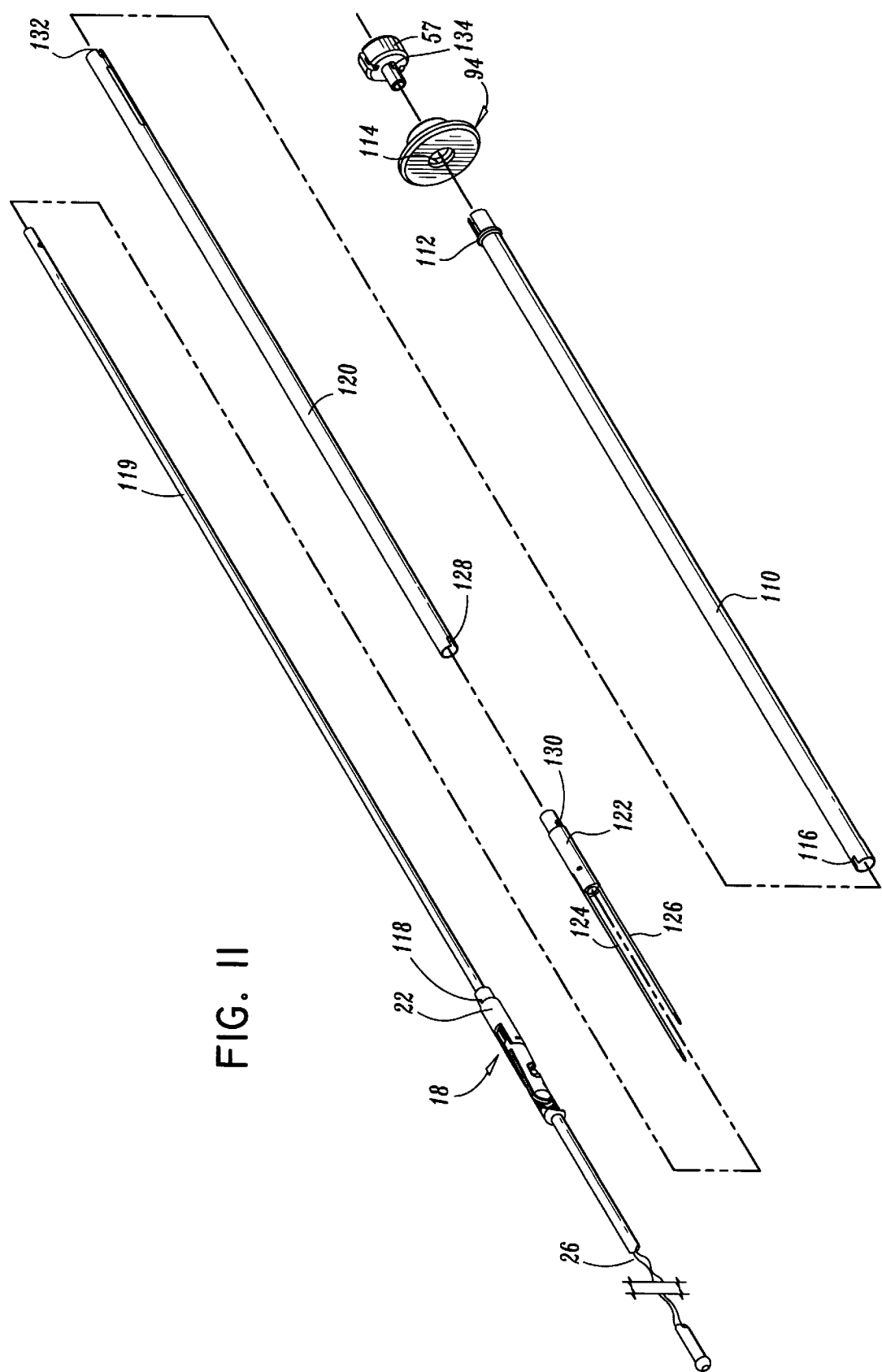
FIG. 11 is a perspective view with parts separated illustrating the components of the elongate body of the apparatus.

Referring to FIGS. 11–13, in conjunction with FIGS. 4–5, the various components of the deployment and actuation assemblies positioned within elongate body 14 will now be described. Elongate body portion 14 preferably includes an outer sleeve 110 connected to and extending distally from distal nose piece 94. Outer sleeve 110 includes a flange 112 which is positionable within a recess 114 formed in distal nose piece 94 to effect the mounting of these two components. At its distal end, outer sleeve 110 supports jaw support 18. In order to retain and properly orient jaw support 18, outer sleeve 110 is formed with a notch 116 at its distal end for receipt of a projection 118 on jaw support 18 to ensure proper alignment thereof during assembly. A deployment rod 119 extends through outer sleeve 110. Deployment rod 119 is connected to deployment extension 82 through pin 117 (FIG. 4) at its proximal end. Distal movement of deployment rod 119 as effectuated by distal movement of deployment member 56 causes deployment of the jaw mechanism 16 as will be appreciated from the description provided hereinbelow.

With continued reference to FIGS. 11–13, a suture engaging assembly is provided to pierce tissue sections and draw the length of suture 26 back through the tissue sections for tie off. The suture engaging assembly includes drive sleeve 120, drive hub 122 connected to a distal end of the drive sleeve 120 and suture engaging members 124, 126 extending from a proximal end of drive hub 122. Drive sleeve 120 and drive hub 122 are slidably positioned within outer sleeve 110 as depicted in FIGS. 13A and 13B. Suture engaging member 124 is configured to engage a free end of suture 26 positioned within stationary jaw 20 while suture engaging member 126 is configured to engage an opposing free end of suture 26 positioned within movable jaw 22. Preferably, drive hub 122 is affixed to the distal end of drive sleeve 120 by means of a notch 128 and projection 130 arrangement.

The suture engaging assembly also includes drive collar 57 which is also connected to drive sleeve 120 through a notch and groove arrangement. Preferably, as shown, a notch 132 formed in the proximal end of drive sleeve 120 is configured to engage a corresponding projection 134 on drive collar 57. As noted hereinabove and depicted in FIG. 5, drive collar 57 is connected to deployment member 56 through drive bars 50. Thus, by actuating drive collar 57 distally, drive sleeve 120 and suture engaging members 124, 126 are advanced distally.

Figures 14, 15:
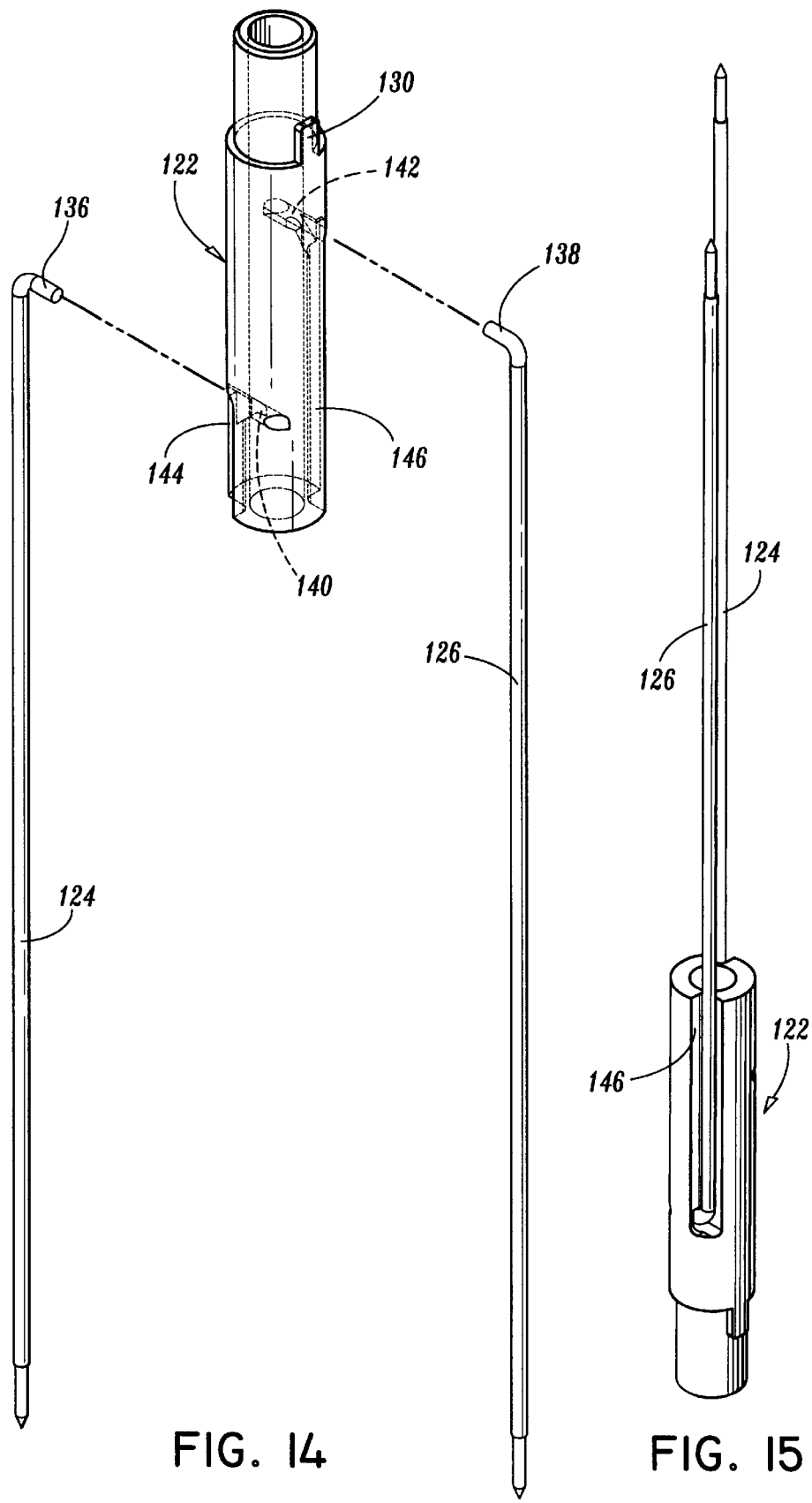
FIG. 14 is a perspective view with parts separated of a drive hub and a pair of suture engaging members of the actuator assembly.
FIG. 15 is a perspective view of the drive hub and suture engaging members in an assembled configuration.

As best depicted in FIGS. 14–15, in view of FIG. 13, suture engaging members or arms 124, 126 include L-shaped proximal ends 136, 138 which are configured to be positioned within offset, transverse bores 140, 142, respectively, formed within drive hub 122. Bore 142 is positioned proximally of bore 140. Bores 140, 142 are offset within drive hub 122 so that deployment rod 119 may slide freely within a bore of drive hub 122. Longitudinal grooves 144, 146 extend distally from bores 140, 142 respectively and are configured to receive suture engaging members 124, 126 such that drive hub 122 has an uniform outer diameter. As shown, suture engaging members 124, 126 are preferably of unequal length. Further, it should be noted that suture engaging member 126 is formed of a flexible material which allows suture engaging member 126 to bend as it moves through deployed movable jaw 22. Suture engaging members 124, 126 include pointed needled ends which are dimensioned to penetrate the tissue sections.

Figure 16:
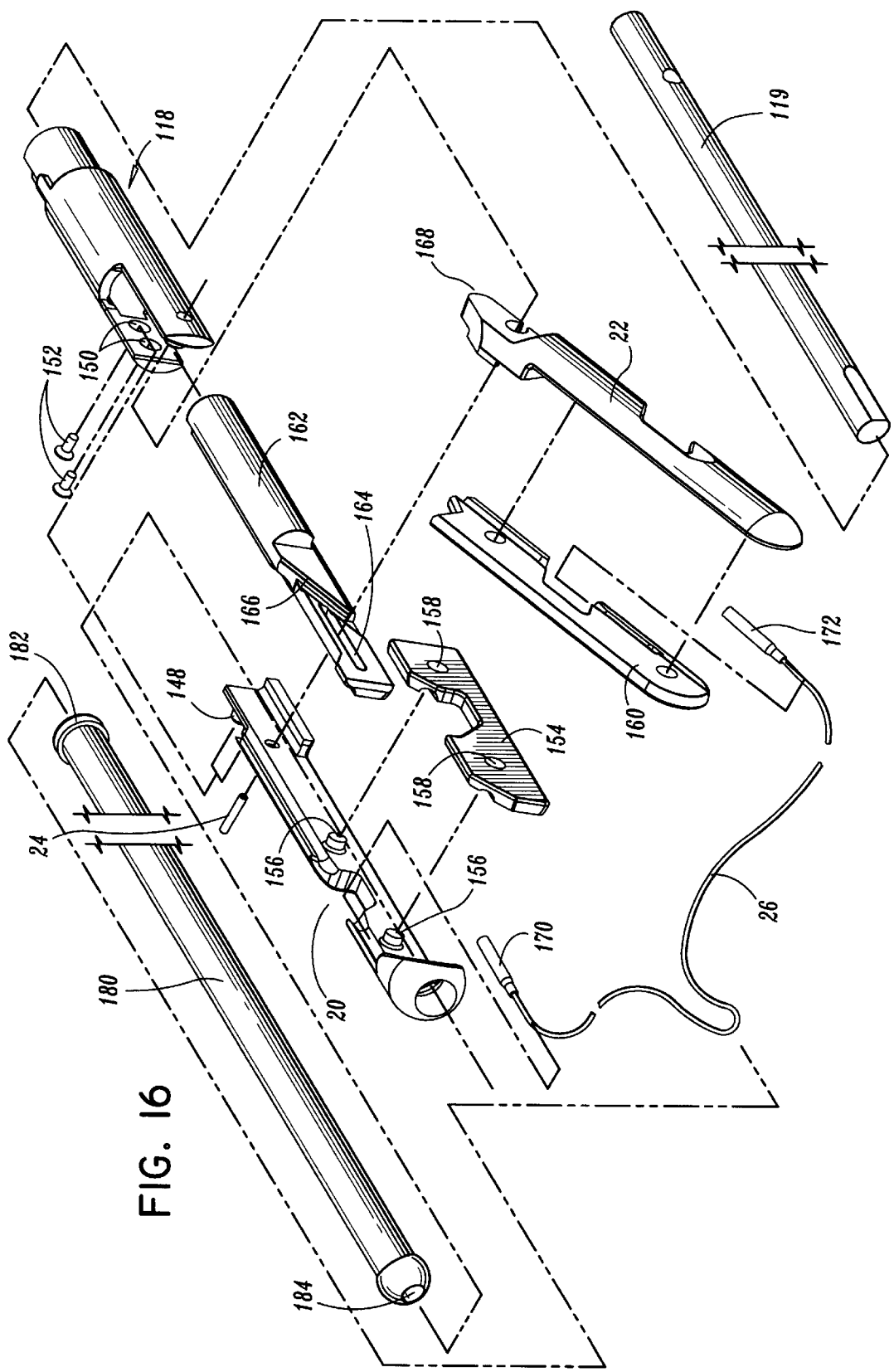
FIG. 16 is a perspective view with parts separated of the jaw assembly and the suture assembly associated therewith.

With reference now to FIG. 16, stationary jaw 20 is affixed to jaw support 18 and include mount tubes 148 which are configured to be positioned within mount holes 150 formed in jaw support 18. Rivets 152 firmly mount tubes 148 within mount holes 150. Stationary jaw 20 further defines a suture mount 154 which is mountable to the stationary jaw 20 through a mount projection 156 and mount hole 158 arrangement. Movable jaw 22 is, as indicated above, pivotally mounted to jaw support 18 and to the proximal end of stationary jaw 20 about pivot pin 24. Movable jaw 22 also defines suture mount 160 which is affixed to the movable jaw 22 through a mount projection and mount hole arrangement similar to that described with stationary jaw 20.

Referring still to FIG. 16, a deployment cam 162 extends through the bore of jaw support 18 where it is connected to deployment rod 119 (see also FIG. 13). Deployment cam 162 includes a longitudinal slot 164 which receives pivot pin 24. Longitudinal slot 164 is elongated to accommodate translation of deployment cam 162. Deployment cam 162 defines camming surface 166 which engages a corresponding camming surface 168 of movable jaw 22 to move the jaw between the open and closed positions.

Suture 26 has ferrules 170, 172 affixed to free ends thereof. Length of suture 26 may be any suitable suture fabricated from, but not limited to, silk, nylon, cotton, polyester, polypropylene, stainless steel, natural materials such as catgut, synthetic polymers having glycolic acid ester linkages. The sutures may be monofilamentary or braided, absorbable or non-absorbable. Ferrules 170, 172 are generally rigid tubes which attach to the free ends of length of suture 26 with use of adhesives, crimping operations, etc. As depicted in FIGS. 17A and 17B, ferrule 170 is preferably positioned within longitudinal bore 174 defined between stationary jaw 20 and suture mount 154 (FIG. 17A). Ferrule 172 is positioned within longitudinal bore 176 defined between movable jaw 22 and suture mount 160. (FIG. 17B).

With reference again to FIG. 16, a suture guide tube 180 is mounted to the distal end of stationary jaw 20. In a preferred arrangement, the proximal end of guide tube 180 is received within a bore of stationary 20 and includes a flange 182 which engages corresponding structure within the stationary jaw 20 to mount the guide tube 180. Suture guide tube 180 is intended to be positioned within the blood vessel and has a traumatic bulbed end portion 184. Suture guide tube 180 can include one or more bores which accommodate the length of suture material 26. Preferably, guide tube 180 has a plurality of bores and suture 26 is disposed longitudinally within each bore, thereby decreasing the length of tube 180 necessary to store the suture.

OPERATION OF THE APPARATUS

The operation of surgical apparatus 10 will now be discussed in conjunction with the use thereof for enclosing a wound formed in a tissue section, for example, a blood vessel. Specifically, apparatus 10 will be discussed in conjunction with the use thereof for enclosing an opening in a femoral artery subsequent to an angioplasty or angiography procedure. The initial position of apparatus 10 is best depicted in FIG. 4.

Figure 19:
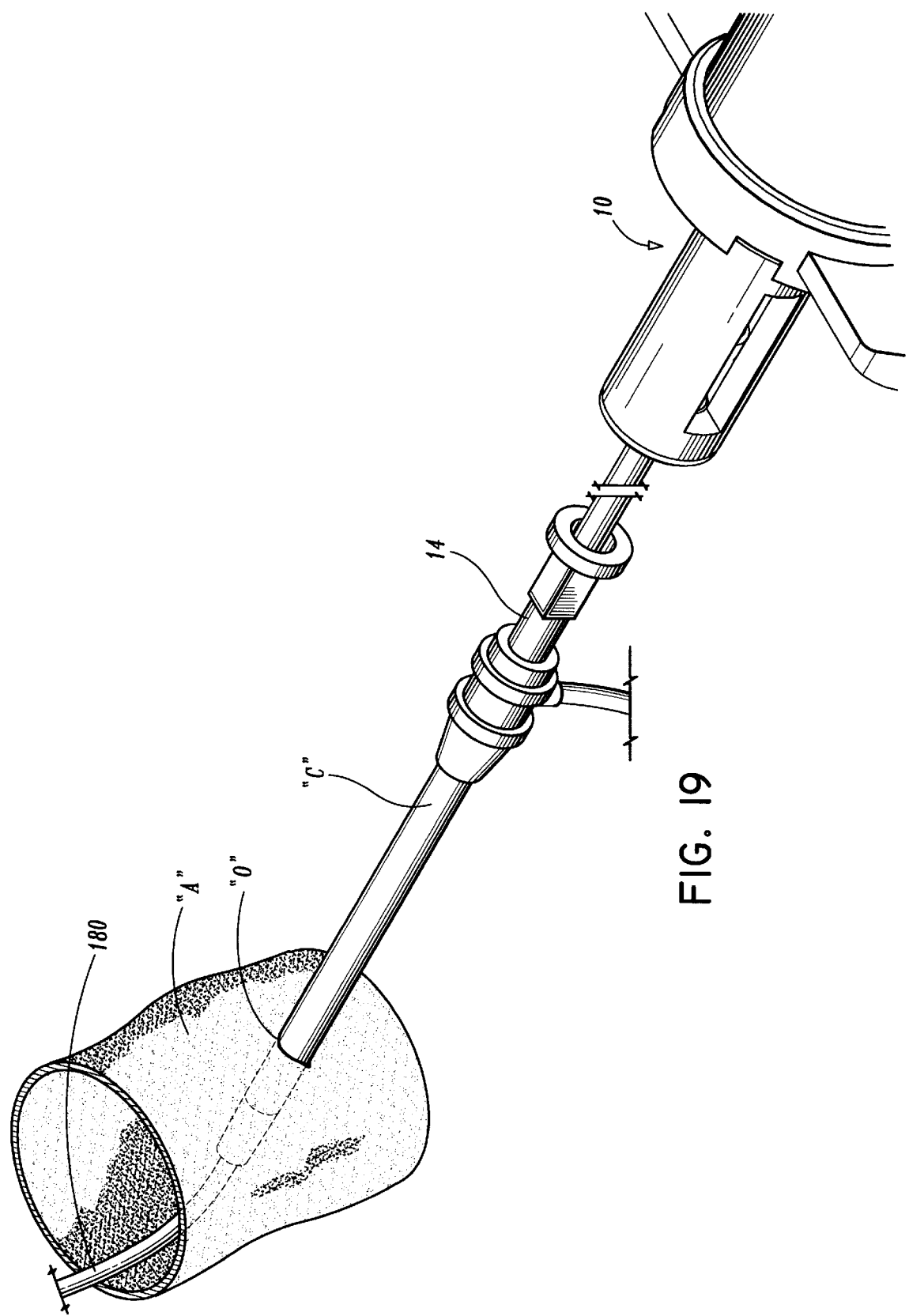
FIG. 19 is a perspective view illustrating insertion of a cannula and the apparatus of FIG. 1 into an opening in the wall of a femoral artery.

Referring now to FIGS. 18 and 19, with surgical apparatus 10 in the above-described initial position, surgical apparatus 10 is introduced through a cannula C which has been placed through a puncture P in a patient. As specifically shown in FIG. 19, surgical apparatus 10, and specifically elongate body 14 is inserted through introducer I which has been prepositioned within an opening O in the femoral artery A. Preferably, suture guide tube 180 is positioned within the artery "A". It is to be noted that guide tube 180 is sufficiently flexible to follow the curved path of the artery.

Figure 20:
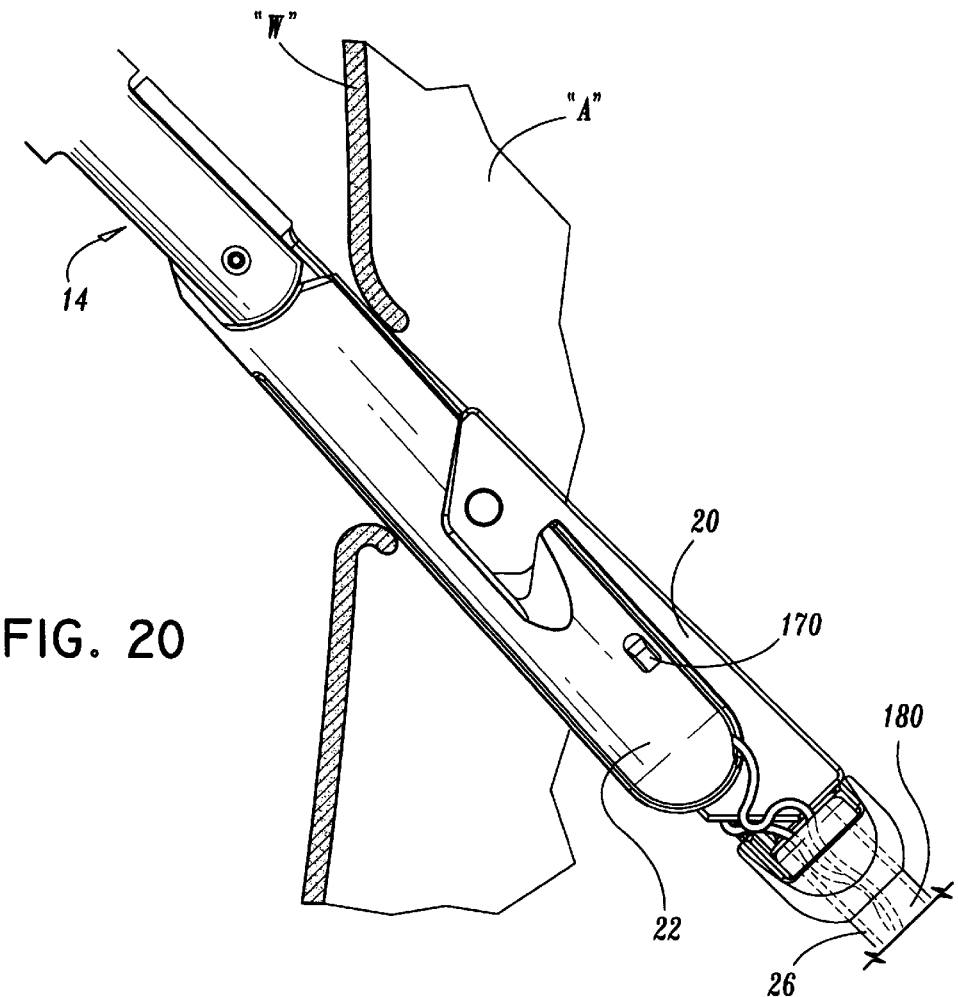
FIG. 20 is a perspective view illustrating the positioning of the jaw assembly within the wall of the femoral artery.

With reference now to FIG. 20, elongate body 14 is inserted partially through opening "O" in a wall "W" of femoral artery "A" such that stationary jaw 20 and movable jaw 22 are at least partially positioned within an interior of femoral artery "A". Preferably, the jaw mechanism is inserted such that ferrules 170, 172 secured by suture mounts 154, 160 are disposed within the interior of the artery "A".

Figure 21:
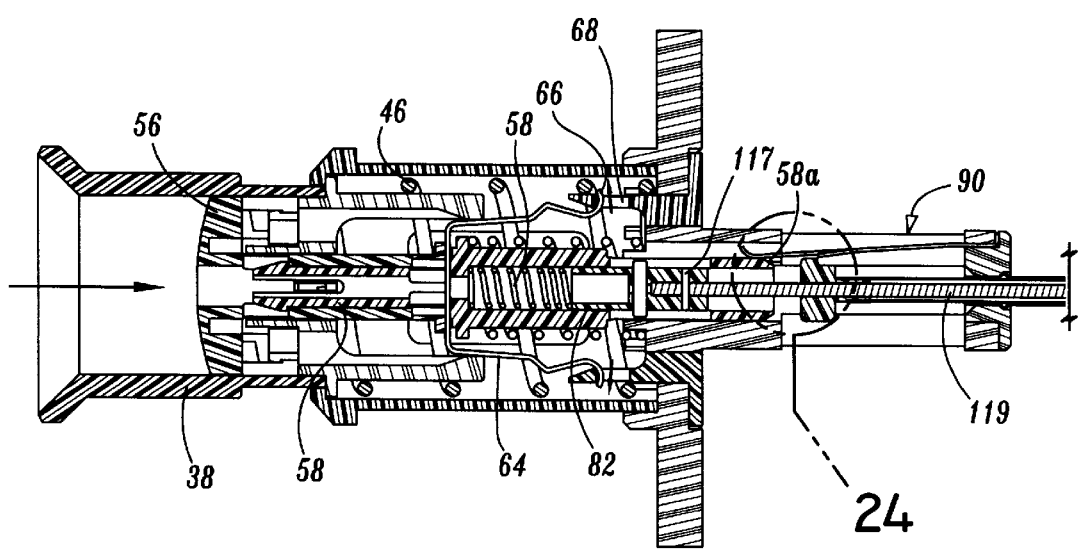
FIG. 21 is a sectional view of the handle of the apparatus of FIG. 1 illustrating activation of the deployment button of the deployment assembly.
Figure 23:
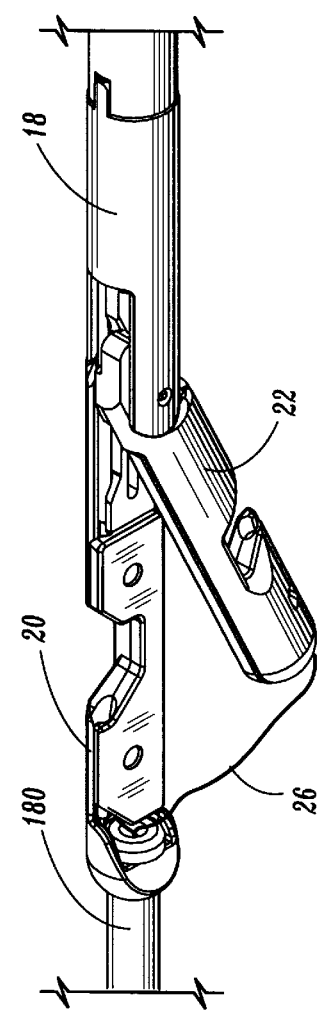
FIG. 23 is a perspective view illustrating the relationship between the movable jaw and the stationary jaw in a deployed position.
Figure 22:
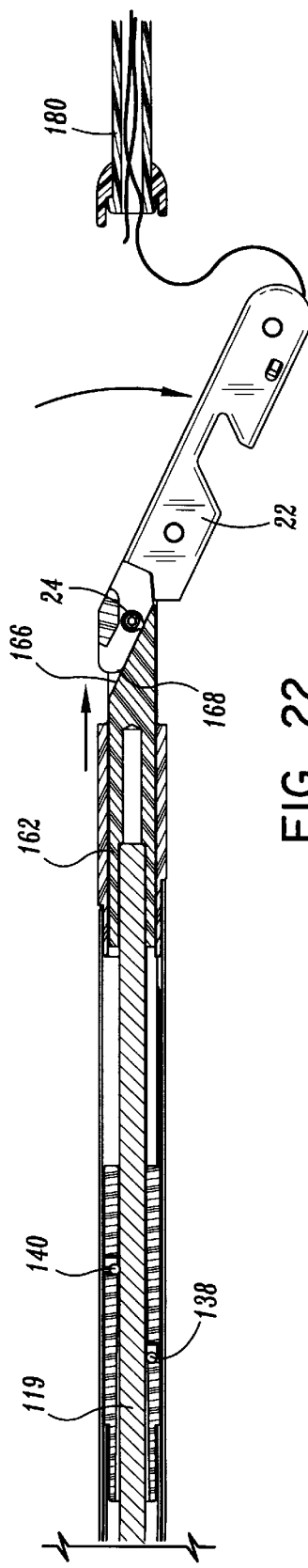
FIG. 22 is a sectional view of the distal end of the apparatus of FIG. 1 illustrating camming of the movable jaw during movement of the deployment button.

Referring now to FIG. 21, in order to deploy the jaw structure, the deployment member 56 is fully depressed within actuator 38 to thereby drive deployment plunger 58 and deployment extension 82 mounted within the bore of plunger 58 distally through engagement with biasing spring 88. More particularly, movement of deployment plunger 58 causes coil spring 88 contained therein to bias deployment extension 82 distally due to engagement of the spring 88 with the proximal end of the extension 82. Deployment extension 82 is movable relative to deployment plunger 58 via traversing movement of pins 84 within slots 86 of the plunger 58. Such distal movement of deployment extension 82 causes deployment rod 119 also to move in a distal direction. As depicted in FIGS. 22–23, upon movement of deployment rod 119 to a distal position, deployment cam 162 is also moved distally from the initial position depicted in FIG. 13, which causes engagement of camming surface 166 of the cam 162 with camming surface 168 of moveable jaw 22. Jaw 22 is thus cammed to pivot away from stationary jaw 20 as shown in the figures. It is to be noted that deployment rod 119 may move proximally for a limited distance against the bias of biasing spring 88 during manipulation of the jaw structure within the body vessel to facilitate proper positioning thereof relative to the openings.

Upon complete depression of deployment member 56, latch end portions 66 of latch 64 engage latch recesses 68. Once engaged, latch 64 prevents proximal movement of deployment plunger 58 thus maintaining jaw mechanism 20 in a deployed position.

Figure 24:
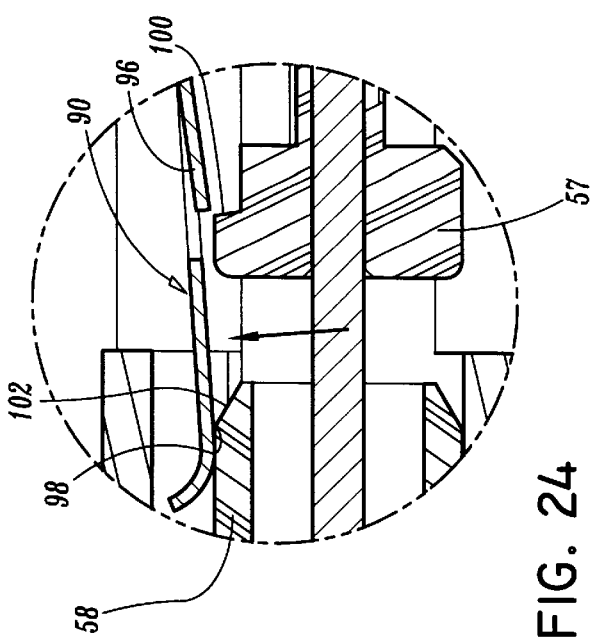
FIG. 24 is an enlarged isolated view of FIG. 21 illustrating release of the lockout member upon actuation of the deployment assembly.

Referring again to FIG. 21, in conjunction with FIG. 24, upon full depression of deployment member 56, in addition to engaging latch member 64, depression of deployment member 56 causes the release of locking finger 96 of spring 90. Specifically, as deployment member 56 is moved to a distalmost position, distal camming surface 102 of deployment plunger 58 engages camming surface 98 of spring 90 thereby biasing locking finger 96 of the spring away from drive collar 57. As locking finger 56 is moved away from drive collar 57, locking finger 96 is disengaged from ledge 100 formed on drive collar 57. Thus, upon a complete depression of deployment member 56, the lockout structure of surgical apparatus 10 is disengaged leaving the suture engaging mechanism of surgical apparatus 10 in condition to be actuated.

Figure 25:
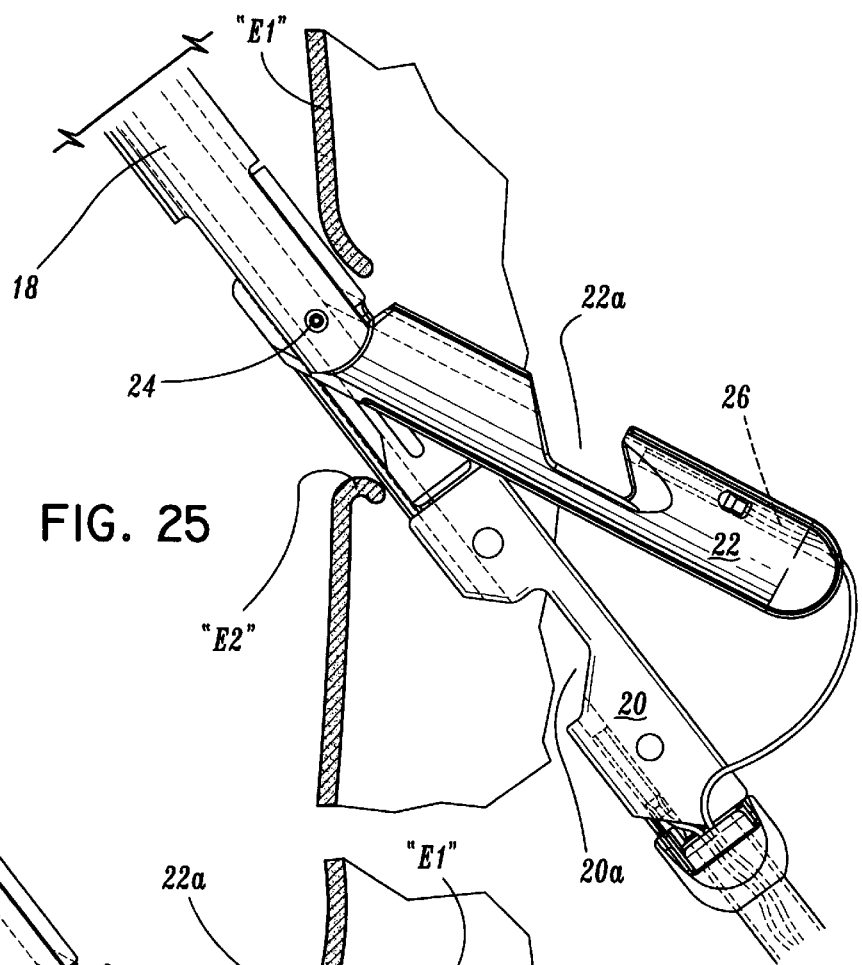
FIG. 25 is a view, partially shown in section, illustrating the positioning of the jaw assembly in the deployed position within the femoral artery.
Figure 26:
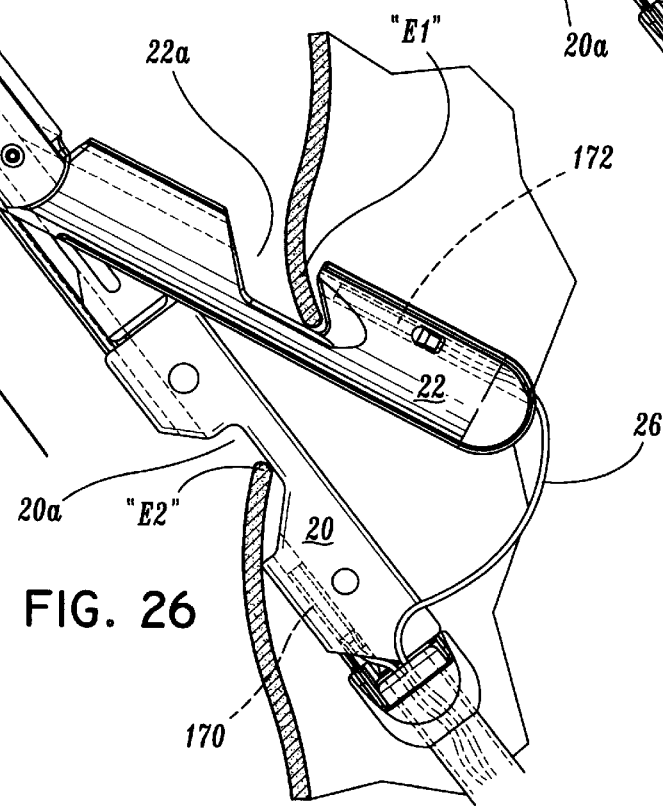
FIG. 26 is a view similar to FIG. 25 illustrating retraction of the distal end of the apparatus of FIG. 1 to engage the walls of the femoral artery with the jaw assembly.

Referring now to FIGS. 25 and 26, once movable jaw 22 has been moved to a deployed position spaced apart from stationary jaw 20, surgical apparatus 10 may be withdrawn slightly through opening O in wall W of femoral artery A thereby causing edge E1 to enter tissue receiving recess 22a of movable jaw 22. Similarly, edge E2 of wall W enters tissue receiving recess 20a of stationary jaw 20.

Figure 28:
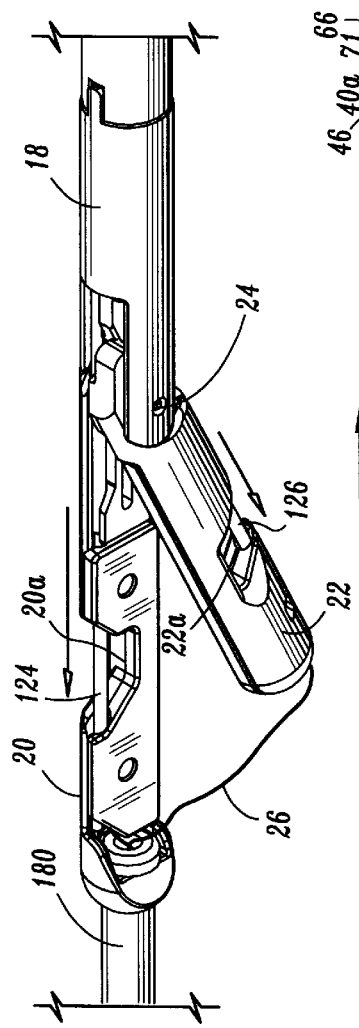
FIG. 28 is a perspective view of the distal end of the apparatus of FIG. 1 during actuation illustrating advancement of the suture engaging members.
Figure 27:
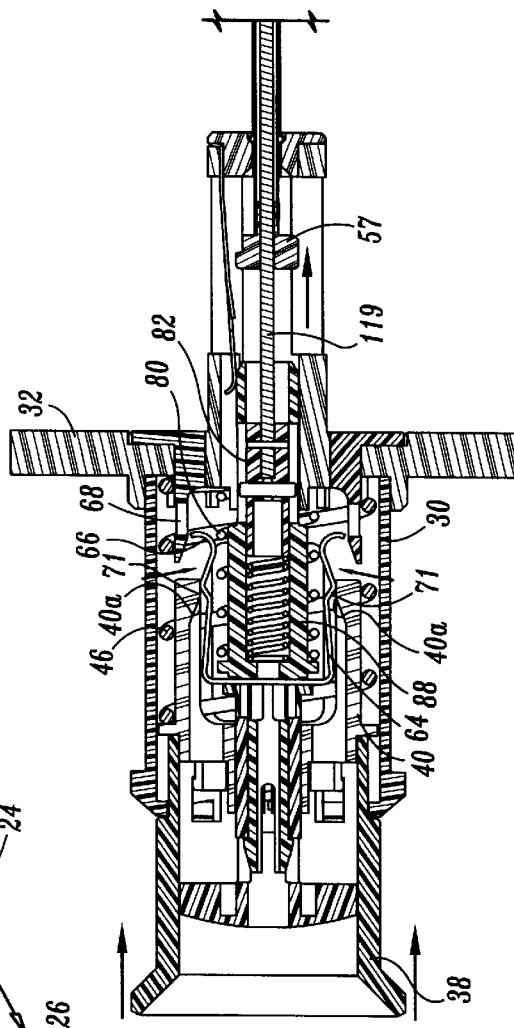
FIG. 27 is a sectional view of the handle of the apparatus of FIG. 1 illustrating actuation of the actuator member of the actuator assembly.
Figure 29:
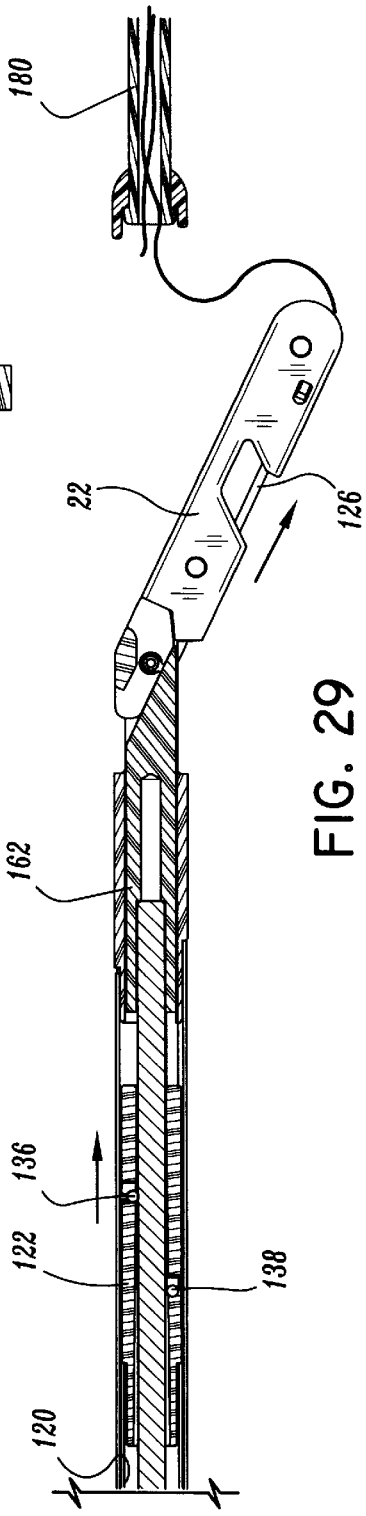
FIG. 29 is a sectional view of the distal end of the apparatus further illustrating advancement of the suture engaging members.
Figure 33:
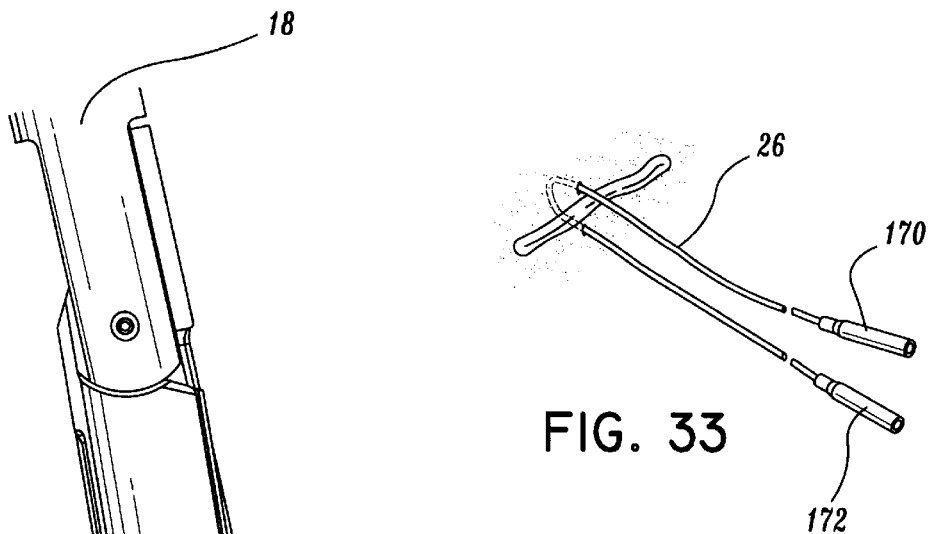
FIG. 33 is a perspective view illustrating the suture assembly after deployment about an opening in the wall of the femoral artery.

Referring now to FIGS. 27–29, in order to actuate surgical apparatus 10, actuator 38 is depressed to a distalmost position within handle cover 30 against the bias of actuator spring 46. As actuator 38 is moved to a distalmost position, it moves drive collar 57 and thus drive sleeve 120 to a distalmost position via the interconnection with drive bars 50 (see FIG. 5). As drive sleeve 120 is moved distally, drive hub 122 mounted to the sleeve 120 is moved distally thereby advancing suture engaging members 124, 126. As depicted in FIG. 30, upon advancement of needle engaging members 124, 126, the penetrating end portions of the members 124, 126 penetrate edges "E1" and "E2" of wall "W" of aorta "A" and pass therethrough to be received within and frictionally engage respective ferrules 170, 172 attached to suture 26. It is to be noted that the engaging members 124, 126 are guided into engagement with ferrules 170, 172 through guide passageways 182, 184 defined within respective jaws 20, 22.

Simultaneously with deployment of suture engaging members 124, 126, depression of actuator 38 causes release of jaw mechanism 16, i.e., permits movable jaw member 22 to return to its initial closed position. In particular, as actuator 38 moves distally, distal camming surfaces 40a on actuator collar 40 engage camming surfaces 71 (see also FIG. 3) on latch member 64. This engagement forces end portions 66 of latch member 64 out of latch recesses 68 thereby freeing latch 64. Once latch 64 is released, deployment plunger 58 is free to move proximally under the influence of coil spring 80 to move deployment rod 119 proximally thereby closing the jaw mechanism 20. It is to be noted that the timing sequence of the mechanism is such that suture engaging members 124, 126 penetrate the tissue before latch 64 is released.

With reference again to FIG. 28, upon release of actuator 38, actuator 38 is biased proximally by spring 46. As depicted in FIG. 31, as actuator 38 moves proximally, suture engaging members 124, 126 are withdrawn proximally thereby drawing ferrules 170, 172 engaged by needle arms 124, 126 proximally. Thus, suture 26 is also withdrawn proximally and the ends of the suture are drawn through the wall of the vessel.

Figure 32:
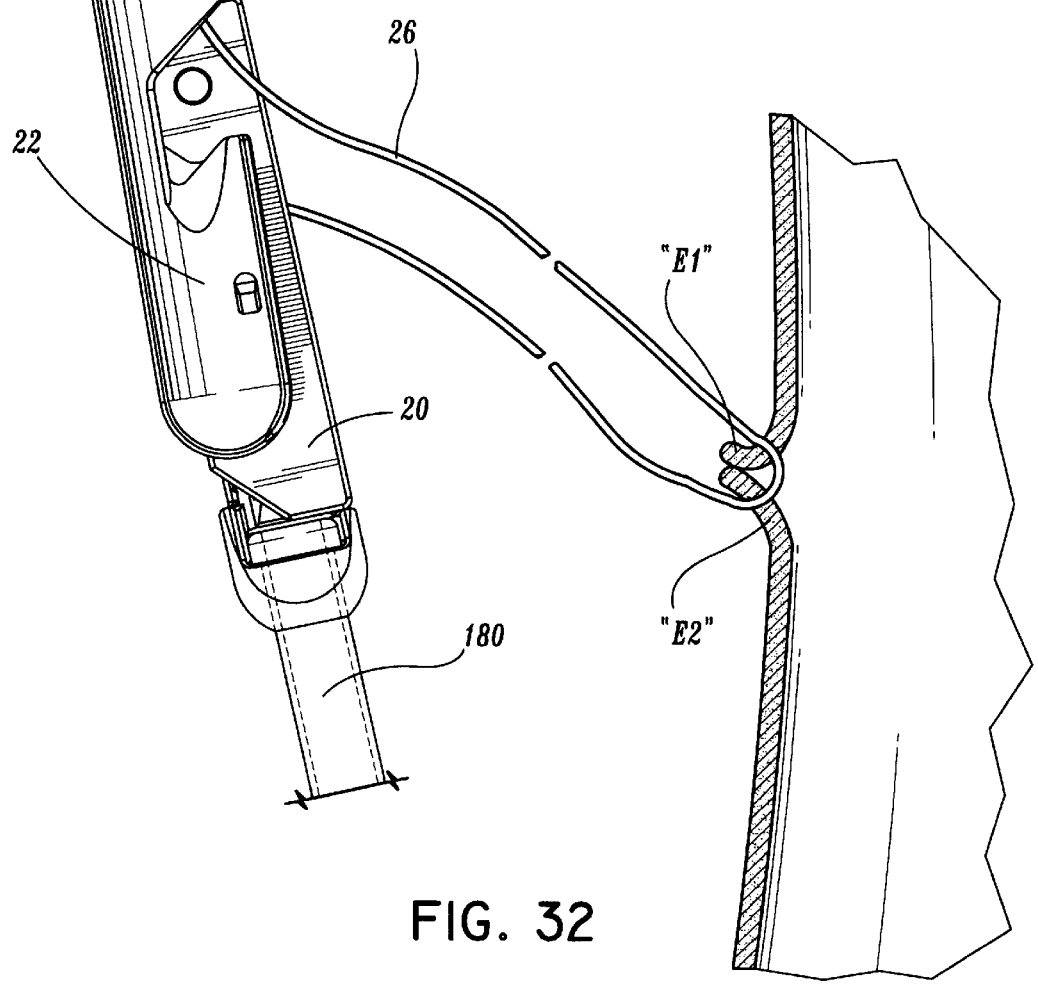
FIG. 32 is a side view illustrating the withdrawal of the distal portion of the apparatus of FIG. 1 from the opening in the wall of the femoral artery and the passage of the suture through the walls of the femoral artery.

Referring now to FIG. 32, as jaws 20, 22 have moved to an undeployed or initial state, elongate body 14 may be withdrawn thereby drawing suture 26 through tissue edges E1 and E2. Thereafter, the free ends of suture 26 with ferrules are available to be tied or otherwise affixed and to close opening O in tissue wall W as shown in FIG. 37. This may be accomplished by various means including for example with use of a suture knot pusher or suture throw rundown tool.

It will be understood that various modifications may be made to the embodiment disclosed herein. For example, various lengths and types of sutures may be employed. Therefore, the above description should not be construed as limiting but merely as an exemplification of a preferred embodiment. Those skilled in the art will envision other modifications within the scope and spirit of the claims appended hereto.

What is claimed is:

1. An apparatus for facilitating wound closure of an opening in tissue, which comprises:

a) a handle portion dimensioned to be gripped by the hand of a user;

b) an elongate body portion connected to the handle portion and extending distally therefrom, the elongate body portion defining a longitudinal axis and having proximal and distal end portions;

c) a jaw mechanism including a stationary jaw affixed to the distal end portion of the elongate body portion and a movable jaw movably mounted to the distal end portion of the elongate body portion and movable between an initial closed position and a deployed open position;

d) a suture assembly including a length of suture supported by the jaw mechanism, the suture assembly at least partially positionable within the opening in the tissue;

e) first and second suture engaging members operatively associated with the stationary jaw and the movable jaw, respectively, the first and second suture engaging members engagable with end portions of the suture;

f) a deployment mechanism operable to move the movable jaw between the initial position and the deployed position; and g) an actuator mechanism operatively associated with the first and second suture engaging members, the actuator mechanism configured to move the first and second suture engaging members from a first position remote from the free ends of the suture to a second position wherein the first and second suture engaging members engage respective end portions of the suture.

2. The apparatus according to claim 1, wherein a lockout mechanism is operatively associated with the deployment mechanism and operatively engageable with the actuator mechanism to prevent actuation of the actuator mechanism, the lockout mechanism being movable to a release position disengaged from the actuator mechanism upon movement of the jaw mechanism to the deployed position to thereby permit actuation of the actuator mechanism.

3. The apparatus according to claim 1, wherein the deployment mechanism includes a latch member engagable with one of the handle and the elongate body portion to maintain the movable jaw in the deployed position.

4. The apparatus according to claim 3, wherein the latch member is adapted to release the one of the handle and the elongate body portion upon movement of the first and second suture engaging members to the second position.

5. The apparatus according to claim 4, wherein the actuator mechanism includes camming structure operatively engagable with the latch member such that the camming structure disengages the latch member from the one of the handle and the elongate body portion upon movement of the first and second suture engaging members to the second position.

6. The apparatus according to claim 4 including a deployment biasing member to normally bias the deployment mechanism to a position corresponding to the initial position of the movable jaw.

7. The apparatus according to claim 1, wherein the suture assembly includes a ferrule attached to each suture end portion, a first ferrule being mounted to the stationary jaw, a second ferrule being mounted to the movable jaw.

8. The apparatus according to claim 7, wherein the first and second suture engaging members have pointed end portions to penetrate tissue.

9. The apparatus according to claim 8, wherein the pointed end portions of the first and second suture engaging members are correspondingly dimensioned to be received within the ferrules of respective suture end portions such that the suture engaging members securely frictionally engage the ferrules, whereby upon proximal movement of the suture engaging members the suture end portions are pulled through the blood vessel wall.

10. The apparatus according to claim 1 including a suture guide tube mounted to the stationary jaw, the suture guide tube accommodating a portion of the length of suture and being dimensioned to be received within the lumen of the blood vessel.

11. An apparatus for facilitating closure of an opening in tissue, which comprises:

a handle;

an elongate body extending distally from the handle, and having proximal and distal end portions, and defining a longitudinal axis;

a jaw assembly mounted to the distal end of the elongate member and having a stationary jaw and a movable jaw, the movable jaw movable between an initial position adjacent the stationary jaw such that the stationary jaw and the movable jaw are configured to fit through an opening in tissue to a deployed position wherein the movable jaw is spaced apart from the stationary jaw, the stationary jaw and the movable jaw each defining a recess for receipt of an edge of tissue forming the opening in the tissue;

a suture assembly mounted to the jaw assembly, the suture assembly including a length of suture having first and second suture end portions; and first and second suture engaging members movably mounted within the stationary and the movable jaw such that the first suture engaging member is movable to traverse the recess in the stationary jaw to engage the first suture end portion and the second suture engaging member is movable to traverse the recess in the movable jaw to engage the second suture end portion.

12. The apparatus according to claim 11, wherein the first and second suture engaging members include needled end portions, the needled end portions configured to penetrate the tissue edges positioned in the recesses when the suture engaging members are moved from a first position remote from the recesses to a second position traversing the recesses.

13. The apparatus according to claim 12, wherein the suture end portions include ferrules configured for frictional engagement with the needled end portions of the first and second suture engaging members as the engaging members are moved from the first position to the second position.

14. The apparatus according to claim 11, further comprising a lockout member, the lockout member preventing movement of the suture engaging members until the movable jaw is moved to the deployed position.

15. The apparatus according to claim 11 including a deployment member mounted to the handle and in operative engagement with the jaw assembly to move the movable jaw between the initial position and the deployed position.

16. The apparatus according to claim 14 including an actuator member mounted to the handle and in operative engagement with the first and second suture engaging members for causing movement thereof.

17. A method for facilitating closure of an opening in a tissue, comprising the steps of:

introducing an elongate body of a surgical apparatus through an opening in a tissue section such that a distal and portion of the surgical apparatus is disposed within a space behind the opening in the tissue section, the distal end portion including a stationary jaw and a movable jaw, the stationary and movable jaws supporting free ends of a length of suture thereon;

moving a distal end of the movable jaw away from a distal end of the stationary jaw;

advancing first and second suture engaging members operatively associated with the elongate body through opposed sides of the opening in the tissue section;

engaging the first and second suture engaging members with respective free ends of the length of suture;

retracting the first and second suture engaging members such that the free ends of the length of suture engaged by the first and second suture engaging members are drawn through the opposed edges of tissue and an intermediate portion of the length of suture extends across the opening; and securing the free end portions of the length of suture to facilitate closure of the opening.

\* \* \* \* \*